(12) United States Patent
Mason et al.

(10) Patent No.: US 11,282,604 B2
(45) Date of Patent: Mar. 22, 2022

(54) METHOD AND SYSTEM FOR USE OF TELEMEDICINE-ENABLED REHABILITATIVE EQUIPMENT FOR PREDICTION OF SECONDARY DISEASE

(71) Applicant: ROM TECHNOLOGIES, INC., Brookfield, CT (US)

(72) Inventors: Steven Mason, Las Vegas, NV (US); Daniel Posnack, Fort Lauderdale, FL (US); Peter Arn, Roxbury, CT (US); Wendy Para, Las Vegas, NV (US); S. Adam Hacking, Nashua, NH (US); Micheal Mueller, Oil City, PA (US); Joseph Guaneri, Merrick, NY (US); Jonathan Greene, Denver, CO (US)

(73) Assignee: ROM Technologies, Inc., Brookfield, CT (US)

( * ) Notice: Subject to any disclaimer, the term of this patent is extended or adjusted under 35 U.S.C. 154(b) by 0 days.

(21) Appl. No.: 17/147,445

(22) Filed: Jan. 12, 2021

(65) Prior Publication Data
US 2021/0134457 A1    May 6, 2021

Related U.S. Application Data

(63) Continuation-in-part of application No. 17/021,895, filed on Sep. 15, 2020, now Pat. No. 11,071,597.
(Continued)

(51) Int. Cl.
*A61B 5/0205* (2006.01)
*G16H 40/67* (2018.01)
(Continued)

(52) U.S. Cl.
CPC .......... *G16H 40/67* (2018.01); *A61B 5/0022* (2013.01); *A61B 5/02055* (2013.01); *A61H 1/02* (2013.01);
(Continued)

(58) Field of Classification Search
CPC ... A61B 5/0022; A61B 5/02055; A61B 5/021; A61B 5/024; A61B 5/0816;
(Continued)

(56) References Cited

U.S. PATENT DOCUMENTS

| 5,429,140 A | 7/1995 | Burdea et al. |
| 6,182,029 B1 | 1/2001 | Friedman |

(Continued)

FOREIGN PATENT DOCUMENTS

| CA | 2698078 A1 | 3/2010 |
| CN | 112603295 A | 2/2003 |

(Continued)

OTHER PUBLICATIONS

International Search Report and Written Opinion for International Application No. PCT/US2021/032807, dated Sep. 6, 2021, 11 pages.

*Primary Examiner* — George Manuel
(74) *Attorney, Agent, or Firm* — Dickinson Wright, PLLC; Stephen A. Mason; Jonathan H. Harder

(57) ABSTRACT

A computer-implemented system may include a treatment device configured to be manipulated by a user while the user is performing a treatment plan, a patient interface comprising an output device configured to present telemedicine information associated with a telemedicine session, and a first computing device configured to: receive treatment data pertaining to the user while the user uses the treatment device to perform the treatment plan; identify at least one aspect of the at least one measurement pertaining to the user associated with a first treatment device mode of the treatment device; determine whether the at least one aspect of the measurement correlates with a secondary condition of the user; and, in response to a determination that the at least one aspect of the at least one measurement is correlated with the at least one secondary condition of the user, generate sec-
(Continued)

ondary condition information indicating at least the secondary condition.

30 Claims, 13 Drawing Sheets

Related U.S. Application Data

(60) Provisional application No. 62/910,232, filed on Oct. 3, 2019.

(51) Int. Cl.
| | |
|---|---|
| *A63B 24/00* | (2006.01) |
| *A61B 5/00* | (2006.01) |
| *G16H 20/30* | (2018.01) |
| *A61H 1/02* | (2006.01) |
| *A63B 21/00* | (2006.01) |
| *G06N 20/00* | (2019.01) |
| *A61B 5/024* | (2006.01) |
| *A61B 5/08* | (2006.01) |
| *A61B 5/021* | (2006.01) |
| *A61B 5/145* | (2006.01) |
| *A63B 22/00* | (2006.01) |

(52) U.S. Cl.
CPC .. *A63B 21/00178* (2013.01); *A63B 21/00181* (2013.01); *A63B 24/0062* (2013.01); *G06N 20/00* (2019.01); *G16H 20/30* (2018.01); *A61B 5/021* (2013.01); *A61B 5/024* (2013.01); *A61B 5/0816* (2013.01); *A61B 5/14542* (2013.01); *A61H 1/0214* (2013.01); *A63B 2022/0094* (2013.01); *A63B 2024/0093* (2013.01)

(58) Field of Classification Search
CPC .... A61B 5/14542; A61H 1/02; A61H 1/0214; A63B 2022/0094; A63B 2024/0093; A63B 21/00178; A63B 21/00181; A63B 24/0062; G06N 20/00; G16H 20/30; G16H 40/67
See application file for complete search history.

(56) References Cited

U.S. PATENT DOCUMENTS

| | | | |
|---|---|---|---|
| 6,273,863 | B1 | 8/2001 | Avni et al. |
| 6,413,190 | B1 | 7/2002 | Wood et al. |
| 6,491,649 | B1 | 12/2002 | Ombrellaro |
| 6,535,861 | B1 | 3/2003 | OConnor et al. |
| 6,602,191 | B2 | 8/2003 | Quy |
| 6,626,805 | B1 | 9/2003 | Lightbody |
| 6,890,312 | B1 | 5/2005 | Priester et al. |
| 7,156,665 | B1 | 1/2007 | OConnor et al. |
| 7,169,085 | B1 | 1/2007 | Killin et al. |
| 7,209,886 | B2 | 4/2007 | Kimmel |
| 7,778,851 | B2 | 8/2010 | Schoenberg et al. |
| 7,809,601 | B2 | 10/2010 | Shaya et al. |
| 7,974,689 | B2 | 7/2011 | Volpe et al. |
| 8,287,434 | B2 | 10/2012 | Zavadsky et al. |
| 8,506,458 | B2 | 8/2013 | Dugan |
| 8,540,515 | B2 | 9/2013 | Williams et al. |
| 8,540,516 | B2 | 9/2013 | Williams et al. |
| 8,556,778 | B1 | 10/2013 | Dugan |
| 8,672,812 | B2 | 3/2014 | Dugan |
| 8,751,264 | B2 | 6/2014 | Beraja et al. |
| 8,784,273 | B2 | 7/2014 | Dugan |
| 8,823,448 | B1 | 9/2014 | Shen |
| 8,979,711 | B2 | 3/2015 | Dugan |
| 9,167,281 | B2 | 10/2015 | Petrov et al. |
| 9,272,185 | B2 | 3/2016 | Dugan |
| 9,311,789 | B1 | 4/2016 | Gwin |
| 9,409,054 | B2 | 8/2016 | Dugan |
| 9,443,205 | B2 | 9/2016 | Wall |
| 9,566,472 | B2 | 2/2017 | Dugan |
| 9,579,056 | B2 | 2/2017 | Rosenbek et al. |
| 9,629,558 | B2 | 4/2017 | Yuen et al. |
| 9,872,087 | B2 | 1/2018 | DelloStritto et al. |
| 9,872,637 | B2 | 1/2018 | Kording et al. |
| 9,914,053 | B2 | 3/2018 | Dugan |
| 9,919,198 | B2 | 3/2018 | Romeo et al. |
| 9,937,382 | B2 | 4/2018 | Dugan |
| 9,939,784 | B1 | 4/2018 | Berardinelli |
| 10,074,148 | B2 | 9/2018 | Cashman et al. |
| 10,130,298 | B2 | 11/2018 | Mokaya et al. |
| 10,155,134 | B2 | 12/2018 | Dugan |
| 10,325,070 | B2 | 6/2019 | Beale et al. |
| 10,327,697 | B1 | 6/2019 | Stein et al. |
| 10,424,033 | B2 | 9/2019 | Romeo |
| 10,430,552 | B2 | 10/2019 | Mihai |
| 10,542,914 | B2 | 1/2020 | Forth et al. |
| 10,572,626 | B2 | 2/2020 | Balram |
| 10,576,331 | B2 | 3/2020 | Kuo |
| 10,660,534 | B2 | 5/2020 | Lee et al. |
| 10,678,890 | B2 | 6/2020 | Bitran et al. |
| 10,685,092 | B2 | 6/2020 | Paparella et al. |
| 10,777,200 | B2 | 9/2020 | Will et al. |
| 10,792,495 | B2 | 10/2020 | Izvorski et al. |
| 10,874,905 | B2 | 12/2020 | Belson et al. |
| 10,931,643 | B1 | 2/2021 | Neumann |
| 11,000,735 | B2 | 5/2021 | Orady et al. |
| 11,045,709 | B2 | 6/2021 | Putnam |
| 11,065,527 | B2 | 7/2021 | Putnam |
| 2002/0160883 | A1 | 10/2002 | Dugan |
| 2003/0036683 | A1 | 2/2003 | Kehr et al. |
| 2003/0109814 | A1 | 6/2003 | Rummertield |
| 2004/0147969 | A1 | 7/2004 | Mann et al. |
| 2005/0049122 | A1 | 3/2005 | Vallone et al. |
| 2006/0064329 | A1 | 3/2006 | Abolfathi et al. |
| 2008/0021834 | A1 | 1/2008 | Holla et al. |
| 2008/0300914 | A1 | 12/2008 | Karkanias et al. |
| 2009/0011907 | A1 | 1/2009 | Radow et al. |
| 2009/0058635 | A1 | 3/2009 | LaLonde et al. |
| 2009/0070138 | A1 | 3/2009 | Langheier et al. |
| 2010/0248899 | A1 | 9/2010 | Bedell et al. |
| 2010/0268304 | A1 | 10/2010 | Matos |
| 2011/0047108 | A1 | 2/2011 | Chakrabarty et al. |
| 2011/0172059 | A1 | 7/2011 | Watterson et al. |
| 2011/0218814 | A1 | 9/2011 | Coats |
| 2011/0275483 | A1 | 11/2011 | Dugan |
| 2012/0065987 | A1 | 3/2012 | Farooq et al. |
| 2012/0190502 | A1 | 7/2012 | Paulus et al. |
| 2012/0295240 | A1 | 11/2012 | Walker et al. |
| 2012/0310667 | A1 | 12/2012 | Altman et al. |
| 2013/0123071 | A1 | 5/2013 | Rhea |
| 2013/0123667 | A1 | 5/2013 | Komatireddy et al. |
| 2013/0231947 | A1* | 9/2013 | Shusterman ....... A61B 5/02055 705/2 |
| 2013/0296987 | A1 | 11/2013 | Rogers et al. |
| 2014/0006042 | A1 | 1/2014 | Keefe et al. |
| 2014/0011640 | A1 | 1/2014 | Dugan |
| 2014/0155129 | A1 | 6/2014 | Dugan |
| 2014/0172460 | A1 | 6/2014 | Kohli |
| 2014/0188009 | A1 | 7/2014 | Lange et al. |
| 2014/0194250 | A1 | 7/2014 | Reich et al. |
| 2014/0207264 | A1 | 7/2014 | Quy |
| 2014/0246499 | A1 | 9/2014 | Proud et al. |
| 2014/0257837 | A1 | 9/2014 | Walker et al. |
| 2014/0309083 | A1 | 10/2014 | Dugan |
| 2014/0315689 | A1 | 10/2014 | Vauquelin et al. |
| 2014/0322686 | A1 | 10/2014 | Kang |
| 2015/0088544 | A1 | 3/2015 | Goldberg |
| 2015/0151162 | A1 | 6/2015 | Dugan |
| 2015/0158549 | A1 | 6/2015 | Gros et al. |
| 2015/0161331 | A1 | 6/2015 | Oleynik |
| 2015/0339442 | A1 | 11/2015 | Oleynik |
| 2015/0341812 | A1 | 11/2015 | Dion et al. |
| 2016/0117471 | A1 | 4/2016 | Belt et al. |
| 2016/0140319 | A1 | 5/2016 | Stark et al. |
| 2016/0151670 | A1 | 6/2016 | Dugan |
| 2016/0166881 | A1 | 6/2016 | Ridgel et al. |
| 2016/0275259 | A1 | 9/2016 | Nolan et al. |

(56) References Cited

U.S. PATENT DOCUMENTS

| | | |
|---|---|---|
| 2016/0302721 A1 | 10/2016 | Wiedenhoefer et al. |
| 2016/0317869 A1 | 11/2016 | Dugan |
| 2016/0322078 A1 | 11/2016 | Bose et al. |
| 2017/0004260 A1 | 1/2017 | Moturu et al. |
| 2017/0046488 A1 | 2/2017 | Pereira |
| 2017/0095692 A1 | 4/2017 | Chang et al. |
| 2017/0095693 A1 | 4/2017 | Chang et al. |
| 2017/0106242 A1 | 4/2017 | Dugan |
| 2017/0136296 A1 | 5/2017 | Barrera et al. |
| 2017/0143261 A1 | 5/2017 | Wiedenhoefer et al. |
| 2017/0147789 A1 | 5/2017 | Wiedenhoefer et al. |
| 2017/0181698 A1 | 6/2017 | Wiedenhoefer et al. |
| 2017/0190052 A1 | 7/2017 | Jaekel et al. |
| 2017/0209766 A1 | 7/2017 | Riley et al. |
| 2017/0243028 A1 | 8/2017 | LaFever et al. |
| 2017/0278209 A1 | 9/2017 | Olsen et al. |
| 2017/0282015 A1 | 10/2017 | Wicks et al. |
| 2017/0300654 A1 | 10/2017 | Stein et al. |
| 2017/0312614 A1 | 11/2017 | Tran et al. |
| 2017/0329917 A1 | 11/2017 | McRaith et al. |
| 2017/0344726 A1 | 11/2017 | Duffy et al. |
| 2017/0360586 A1 | 12/2017 | Dempers et al. |
| 2017/0368413 A1 | 12/2017 | Shavit |
| 2018/0052962 A1 | 2/2018 | Van Der Koijk et al. |
| 2018/0056104 A1 | 3/2018 | Cromie et al. |
| 2018/0075205 A1 | 3/2018 | Moturu et al. |
| 2018/0078843 A1 | 3/2018 | Tran et al. |
| 2018/0085615 A1 | 3/2018 | Astolfi et al. |
| 2018/0102190 A1 | 4/2018 | Hogue et al. |
| 2018/0200577 A1 | 7/2018 | Dugan |
| 2018/0220935 A1 | 8/2018 | Tadano et al. |
| 2018/0240552 A1 | 8/2018 | Tuyl et al. |
| 2018/0263530 A1 | 9/2018 | Jung |
| 2018/0271432 A1 | 9/2018 | Auchinleck et al. |
| 2018/0280784 A1 | 10/2018 | Romeo et al. |
| 2018/0330058 A1 | 11/2018 | Bates |
| 2018/0330824 A1 | 11/2018 | Athey et al. |
| 2018/0373844 A1 | 12/2018 | Ferrandez-Escamez et al. |
| 2019/0019578 A1 | 1/2019 | Vaccaro |
| 2019/0060708 A1 | 2/2019 | Fung |
| 2019/0065970 A1 | 2/2019 | Bonutti et al. |
| 2019/0066832 A1 | 2/2019 | Kang et al. |
| 2019/0076701 A1 | 3/2019 | Dugan |
| 2019/0088356 A1 | 3/2019 | Oliver et al. |
| 2019/0115097 A1 | 4/2019 | Macoviak et al. |
| 2019/0126099 A1 | 5/2019 | Hoang |
| 2019/0134454 A1 | 5/2019 | Mahoney et al. |
| 2019/0167988 A1 | 6/2019 | Shahriari et al. |
| 2019/0172587 A1 | 6/2019 | Park et al. |
| 2019/0175988 A1 | 6/2019 | Volterrani et al. |
| 2019/0200920 A1 | 7/2019 | Tien et al. |
| 2019/0209891 A1 | 7/2019 | Fung |
| 2019/0244540 A1 | 8/2019 | Errante et al. |
| 2019/0269343 A1 | 9/2019 | Ramos Murguialday et al. |
| 2019/0290964 A1 | 9/2019 | Oren |
| 2019/0304584 A1 | 10/2019 | Savolainen |
| 2019/0307983 A1 | 10/2019 | Goldman |
| 2019/0354632 A1 | 11/2019 | Mital et al. |
| 2020/0005928 A1 | 1/2020 | Daniel |
| 2020/0051446 A1 | 2/2020 | Rubinstein et al. |
| 2020/0093418 A1 | 3/2020 | Kluger et al. |
| 2020/0143922 A1 | 5/2020 | Chekroud et al. |
| 2020/0151595 A1 | 5/2020 | Jayalath et al. |
| 2020/0152339 A1 | 5/2020 | Pulitzer et al. |
| 2020/0160198 A1 | 5/2020 | Reeves et al. |
| 2020/0170876 A1 | 6/2020 | Kapure et al. |
| 2020/0176098 A1 | 6/2020 | Lucas et al. |
| 2020/0197744 A1 | 6/2020 | Schweighofer |
| 2020/0289889 A1 | 9/2020 | Hacking et al. |
| 2020/0293712 A1 | 9/2020 | Potts et al. |
| 2020/0395112 A1 | 12/2020 | Ronner |
| 2020/0401224 A1 | 12/2020 | Cotton |
| 2021/0074178 A1 | 3/2021 | Ilan et al. |
| 2021/0098129 A1 | 4/2021 | Neumann |
| 2021/0128978 A1 | 5/2021 | Gilstrom et al. |
| 2021/0186419 A1 | 6/2021 | Van Ee et al. |
| 2021/0202090 A1 | 7/2021 | ODonovan et al. |
| 2021/0202103 A1 | 7/2021 | Bostic et al. |

FOREIGN PATENT DOCUMENTS

| | | |
|---|---|---|
| CN | 103488880 A | 1/2014 |
| CN | 104335211 A | 2/2015 |
| CN | 105894088 A | 8/2016 |
| CN | 105930668 A | 9/2016 |
| CN | 106127646 A | 11/2016 |
| CN | 107430641 A | 12/2017 |
| CN | 112603295 A | 4/2021 |
| DE | 102018202497 A1 | 8/2018 |
| DE | 102018211212 A1 | 1/2019 |
| DE | 102019108425 B3 | 8/2020 |
| EP | 3688537 A1 | 8/2020 |
| EP | 3731733 A1 | 11/2020 |
| JP | 2003225875 A | 8/2003 |
| JP | 6659831 B2 | 10/2017 |
| JP | 2019134909 A | 8/2019 |
| JP | 6710357 B1 | 6/2020 |
| JP | 2020150987 A1 | 9/2020 |
| JP | 6775757 B1 | 10/2020 |
| JP | 2021026768 A | 2/2021 |
| JP | 2021027917 A | 2/2021 |
| KR | 20020009724 A | 2/2002 |
| KR | 20020065253 A | 8/2002 |
| KR | 20160093990 A | 8/2016 |
| KR | 20170038837 A | 4/2017 |
| KR | 20190011885 A | 2/2019 |
| KR | 101988167 B1 | 6/2019 |
| KR | 10211664 B1 | 7/2019 |
| KR | 102116968 B1 | 3/2020 |
| KR | 20200025290 A | 3/2020 |
| KR | 102162522 B1 | 4/2020 |
| KR | 102142713 B1 | 5/2020 |
| KR | 20200056233 A | 5/2020 |
| KR | 102120828 B1 | 6/2020 |
| KR | 102173553 B1 | 11/2020 |
| KR | 102180079 B1 | 11/2020 |
| KR | 102224618 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102264498 B1 | 6/2021 |
| WO | 2001050387 A1 | 7/2001 |
| WO | 2003043494 | 5/2003 |
| WO | 2018171853 A1 | 9/2018 |
| WO | 2019204876 A1 | 4/2019 |
| WO | 2020075190 A1 | 4/2020 |
| WO | 2020130979 A1 | 6/2020 |
| WO | 2020149815 A2 | 7/2020 |
| WO | 2020245727 A1 | 12/2020 |
| WO | 2020249855 A1 | 12/2020 |
| WO | 2020252599 A1 | 12/2020 |
| WO | 2020256577 A1 | 12/2020 |
| WO | 2021021447 A1 | 2/2021 |
| WO | 2021038980 A1 | 3/2021 |
| WO | 2021061061 A1 | 4/2021 |
| WO | 2021138620 A1 | 7/2021 |

\* cited by examiner

METHOD AND SYSTEM FOR USE OF TELEMEDICINE-ENABLED REHABILITATIVE EQUIPMENT FOR PREDICTION OF SECONDARY DISEASE

CROSS-REFERENCES TO RELATED APPLICATIONS

This Continuation-In-Part Patent Application claims priority to and the benefit of U.S. patent application Ser. No. 17/021,895 filed Sep. 15, 2020, titled "Telemedicine for Orthopedic Treatment", which claims priority to and the benefit of U.S. Provisional Application Patent Ser. No. 62/910,232 filed Oct. 3, 2019, titled "Telemedicine for Orthopedic Treatment", the entire disclosures of which are hereby incorporated by reference.

BACKGROUND

Remote medical assistance, also referred to, inter alia, as remote medicine, telemedicine, telemed, telmed, tel-med, or telehealth, is an at least two-way communication between a healthcare provider or providers, such as a physician or a physical therapist, and a patient using audio and/or audio-visual and/or other sensorial or perceptive (e.g., tactile, gustatory, haptic, pressure-sensing-based or electromagnetic (e.g., neurostimulation) communications (e.g., via a computer, a smartphone, or a tablet).

SUMMARY

An aspect of the disclosed embodiments comprises a computer-implemented system. The computer-implemented system may include a treatment device configured to be manipulated by a user while the user is performing a treatment plan and a patient interface comprising an output device configured to present telemedicine information associated with a telemedicine session. The computer-implemented system may also include a first computing device configured to: receive treatment data pertaining to the user while the user uses the treatment device to perform the treatment plan, wherein the treatment data comprises at least one of at least one characteristic of the user, at least one measurement pertaining to the user, at least one characteristic of the treatment device, and at least one aspect of the treatment plan; identify, using at least one aspect of the treatment data, at least one aspect of the at least one measurement pertaining to the user associated with a first treatment device mode of the treatment device; determine whether the at least one aspect of the at least one measurement pertaining to the user associated with the first treatment device mode of the treatment device correlates with at least one secondary condition of the user, wherein the at least one secondary condition of the user is not a primary condition for which the user is being treated; in response to a determination that the at least one aspect of the at least one measurement pertaining to the user associated with the first treatment device mode of the treatment device is correlated with the at least one secondary condition of the user, generate secondary condition information indicating at least the secondary condition; and write to an associated memory, for access at a second computing device of a healthcare provider, the secondary condition information.

Another aspect of the disclosed embodiments comprises a method that may include receiving treatment data pertaining to a user using a treatment device to perform a treatment plan. The treatment data may include at least one of at least one characteristic of the user, at least one measurement pertaining to the user, at least one characteristic of the treatment device, and at least one aspect of the treatment plan. The method may also include identifying, using at least one aspect of the treatment data, at least one aspect of the at least one measurement pertaining to the user associated with a first treatment device mode of the treatment device. The method may also include determining whether the at least one aspect of the at least one measurement pertaining to the user associated with the first treatment device mode of the treatment device correlates with at least one secondary condition of the user, wherein the at least one secondary condition of the user is not a primary condition for which the user is being treated. The method may also include, in response to a determination that the at least one aspect of the at least one measurement pertaining to the user associated with the first treatment device mode of the treatment device is correlated with the at least one secondary condition of the user, generating secondary condition information indicating at least the secondary condition. The method may also include writing to an associated memory, for access at a computing device of a healthcare provider, the secondary condition information.

Another aspect of the disclosed embodiments includes a system that includes a processing device and a memory communicatively coupled to the processing device and capable of storing instructions. The processing device executes the instructions to perform any of the methods, operations, or steps described herein.

Another aspect of the disclosed embodiments includes a tangible, non-transitory computer-readable medium storing instructions that, when executed, cause a processing device to perform any of the methods, operations, or steps described herein.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

NOTATION AND NOMENCLATURE

Figure 1:
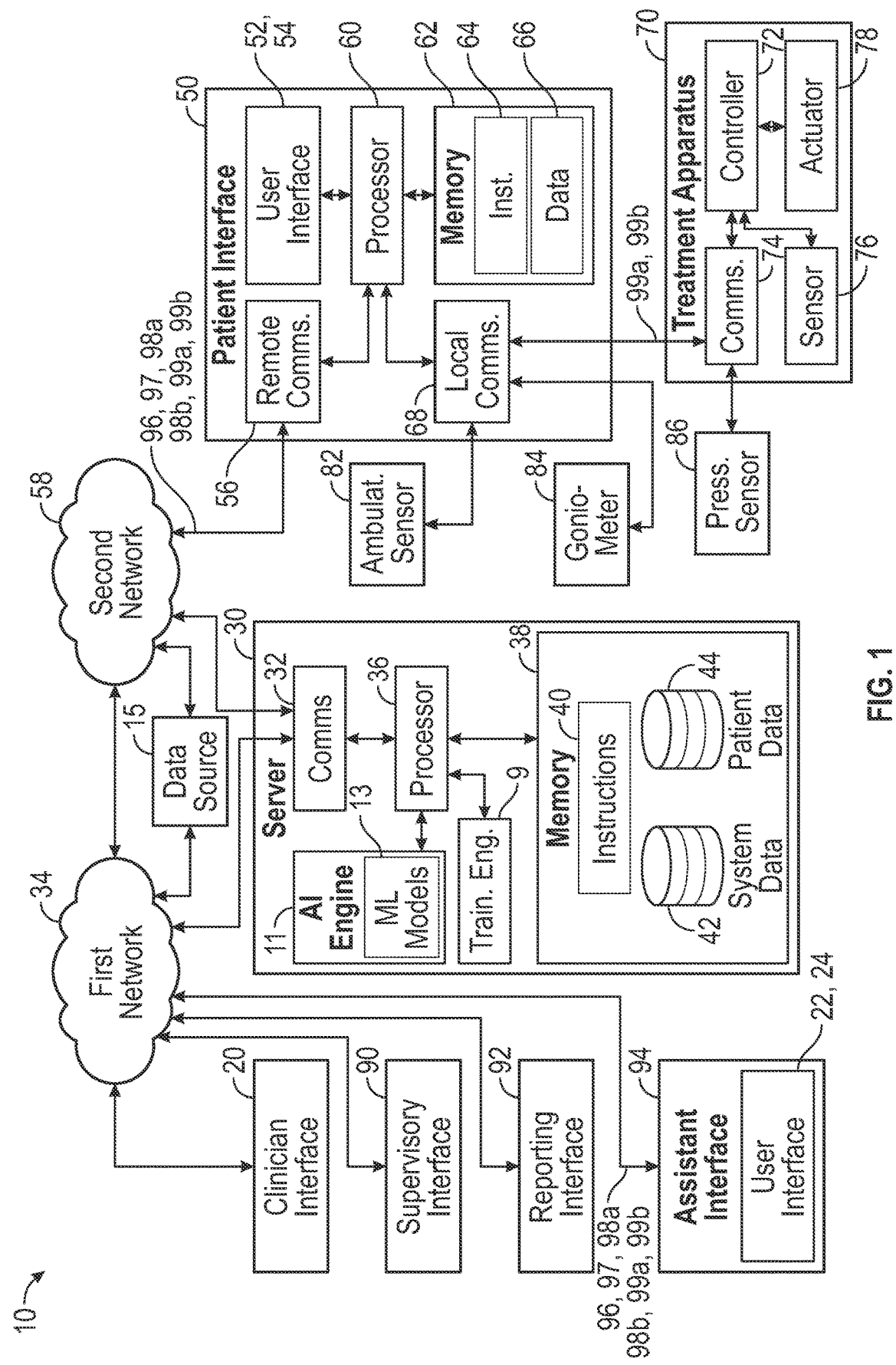
FIG. 1 generally illustrates a block diagram of an embodiment of a computer-implemented system for managing a treatment plan according to the principles of the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols, and each treatment protocol includes one or more treatment sessions. Each treatment session comprises several session periods, with each session period including a particular exercise for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment device, a diet regimen for the patient, a medication regimen for the patient, a sleep regimen for the patient, additional regimens, or some combination thereof.

The terms telemedicine, telehealth, telemed, teletherapeutic, telemedicine, remote medicine, etc. may be used interchangeably herein.

The term "enhanced reality" may include a user experience comprising one or more of augmented reality, virtual reality, mixed reality, immersive reality, or a combination of the foregoing (e.g., immersive augmented reality, mixed augmented reality, virtual and augmented immersive reality, and the like).

The term "augmented reality" may refer, without limitation, to an interactive user experience that provides an enhanced environment that combines elements of a real-world environment with computer-generated components perceivable by the user.

The term "virtual reality" may refer, without limitation, to a simulated interactive user experience that provides an enhanced environment perceivable by the user and wherein such enhanced environment may be similar to or different from a real-world environment.

The term "mixed reality" may refer to an interactive user experience that combines aspects of augmented reality with aspects of virtual reality to provide a mixed reality environment perceivable by the user.

The term "immersive reality" may refer to a simulated interactive user experienced using virtual and/or augmented reality images, sounds, and other stimuli to immerse the user, to a specific extent possible (e.g., partial immersion or total immersion), in the simulated interactive experience. For example, in some embodiments, to the specific extent possible, the user experiences one or more aspects of the immersive reality as naturally as the user typically experiences corresponding aspects of the real-world. Additionally, or alternatively, an immersive reality experience may include actors, a narrative component, a theme (e.g., an entertainment theme or other suitable theme), and/or other suitable features of components.

The term "body halo" may refer to a hardware component or components, wherein such component or components may include one or more platforms, one or more body supports or cages, one or more chairs or seats, one or more back supports, one or more leg or foot engaging mechanisms, one or more arm or hand engaging mechanisms, one or more neck or head engaging mechanisms, other suitable hardware components, or a combination thereof.

As used herein, the term "enhanced environment" may refer to an enhanced environment in its entirety, at least one aspect of the enhanced environment, more than one aspect of the enhanced environment, or any suitable number of aspects of the enhanced environment.

The term "medical action(s)" may refer to any suitable action performed by the medical professional (e.g., or the healthcare professional), and such action or actions may include diagnoses, prescription of treatment plans, prescription of treatment devices, and the making, composing and/or executing of appointments, telemedicine sessions, prescriptions or medicines, telephone calls, emails, text messages, and the like.

As used herein, the terms "correlate," "correlation," and the like may refer to any suitable correlation or correlative relationship, including a correlation coefficient (e.g., a value indicating an amount of correlation) not equal to zero (e.g., not perfect correlation), or any suitable correlation coefficient.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining optimal remote examination procedures to create an optimal treatment plan for a patient having certain characteristics (e.g., vital-sign or other measurements; performance; demographic; psychographic; geographic; diagnostic; measurement- or test-based; medically historic; etiologic; cohort-associative; differentially diagnostic; surgical, physically therapeutic, behavioral, pharmacologic and other treatment(s) recommended; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include characteristics of the patient such as personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment device, an amount of force exerted on a portion of the treatment device, a range of motion achieved on the treatment device, a movement speed of a portion of the treatment device, a duration of use of the treatment device, an indication of a plurality of pain levels using the treatment device, or some combination thereof. The measurement information may include, e.g., a vital sign, a respiration rate, a heartrate, a temperature, a blood pressure, a glucose level or other biomarker, or some combination thereof. It may be desirable to process and analyze the characteristics of a multitude of patients, the treatment plans performed for those patients, and the results of the treatment plans for those patients.

Further, another technical problem may involve distally treating, via a computing device during a telemedicine or telehealth session, a patient from a location different than a location at which the patient is located. An additional technical problem is controlling or enabling the control of, from the different location, a treatment device used by the patient at the location at which the patient is located. Oftentimes, when a patient undergoes rehabilitative surgery (e.g., knee surgery), a healthcare provider may prescribe a treatment device to the patient to use to perform a treatment protocol at their residence or any mobile location or temporary domicile. A healthcare provider may refer to a doctor, physician assistant, nurse, chiropractor, dentist, physical therapist, acupuncturist, physical trainer, coach, personal trainer, a neurologist, a cardiologist, or the like. A healthcare provider may refer to any person with a credential, license, degree, or the like in the field of medicine, physical therapy, rehabilitation, or the like.

When the healthcare provider is located in a different location from the patient and the treatment device, it may be technically challenging for the healthcare provider to monitor the patient's actual progress (as opposed to relying on the patient's word about their progress) using the treatment device, modify the treatment plan according to the patient's progress, adapt the treatment device to the personal characteristics of the patient as the patient performs the treatment plan, and the like.

Typically, the patient may perform, using the treatment device, various aspects of the treatment plan to treat one or more conditions of the patient. For example, the patient may be recovering from an orthopedic surgery, a cardiac surgery, a neurological surgery, a gastrointestinal surgery, a genitourological surgery, a gynecological surgery, or other surgery and may use the treatment device to rehabilitate one or more affected portions of the patient's body. Alternatively, the patient may be recovering from a neurological surgery or a program to treat mental unwellness and may use the treatment device to rehabilitate neurological or other mental responses or brain functions which have a physical manifestation with regard to one or more directly or indirectly affected portions of the patient's body. Alternatively, the patient may be being treated for physical and/or mental conditions associated with post-traumatic stress disorder (PTSD) and may use the treatment device to rehabilitate neurological or other mental responses or brain functions, which have a physical manifestation. Further, the patient, while recovering from post-traumatic stress disorder, may use the treatment device to improve general mental health (e.g., through exercise, goal-oriented activity and achievement, and the like). Alternatively, the patient may be being treated for a somatoform disorder associated with PTSD or other trauma, injury, and the like. The patient may use the treatment device to rehabilitate neurological or other mental responses or brain functions, which have a physical manifestation and/or other mental manifestation. Such conditions may be referred to as primary conditions (e.g., conditions for which the patient uses the treatment device to perform the treatment plan). However, the patient may have one or other conditions of which the healthcare provider caring for the patient and/or the patient is unaware. These may be referred to as secondary conditions (e.g., conditions not currently being treated and/or conditions of which the healthcare provider and/or the patient is unaware). As used herein, "secondary condition" means, without limitation, any condition that is not the primary condition, i.e., a first secondary condition, a second secondary condition, a third secondary condition, etc., or alternatively worded, a secondary condition, a tertiary condition, a quaternary condition, etc.

Similarly, the patient may use the treatment device to strength training aspects of the treatment plan or other strength training plan. However, the patient may have one or more conditions not yet identified by or known to the healthcare provider or the patient. Accordingly, systems and methods, such as those described herein, configured to identify one or more conditions of the patient based, at least in part, on the use of the treatment device by the patient, may be desirable. In some embodiments, the system and methods described herein may be configured to receive treatment data pertaining to a user using a treatment device to perform a treatment plan. The user may include a patient, user, or person using the treatment device to perform various exercises. The user may also include a healthcare professional directing the treatment device to be used by a patient, user or other person, wherein such patient, user or other person is using the treatment device to perform various exercises. The treatment data may include various characteristics of the user, various measurement information pertaining to the user while the user uses the treatment device, various characteristics of the treatment device, the treatment plan, other suitable data, or a combination thereof. In some embodiments, the systems and methods described herein may be configured to receive the treatment data during a telemedicine session.

In some embodiments, while the user uses the treatment device to perform the treatment plan, at least some of the treatment data may correspond to at least some sensor data of a sensor configured to sense various characteristics of the treatment device and/or to obtain the measurement information from the user. Additionally, or alternatively, while the user uses the treatment device to perform the treatment plan, at least some of the treatment data may correspond to at least some sensor data from a sensor associated with a wearable device or other sensing or Internet of Things (IoT) device (which may be near the user but not worn by the user) configured to measure, determine, or obtain the measurement information associated with the user.

The various characteristics of the treatment device may include one or more settings of the treatment device, a current revolutions per time period (e.g., such as one minute) of a rotating member (e.g., such as a wheel) of the treatment device, a resistance setting of the treatment device, other suitable characteristics of the treatment device, or a combination thereof. The measurement information may include one or more vital signs of the user, a respiration rate of the user, a heartrate of the user, a temperature of the user, an SpO2-measurement of the blood oxygen level of the user (e.g., oxygen saturation level), a blood pressure of the user, a glucose level of the user, other suitable measurement information of the user, microbiome related data pertaining to the user, or a combination thereof.

In some embodiments, the systems and methods described herein may be configured to identify, using at least one aspect of the treatment data, at least one aspect of the at least one measurement pertaining to the user associated with a first treatment device mode of the treatment device. The first treatment device mode may include any suitable mode of the treatment device, including those described herein.

In some embodiments, the systems and methods described herein may be configured to determine whether or to what extent the at least one aspect of the at least one measurement pertaining to the user associated with the first treatment device mode of the treatment device correlates with at least one secondary condition of the user. The at least one secondary condition may include any condition for which the user is not being treated while using the treatment device (e.g., conditions not currently being treated and/or conditions of which the healthcare provider and/or the patient is unaware). It should be understood that the systems and methods described herein may use at least one other aspect and/or the at least one aspect of the at least one measurement and/or at least one other measurement pertaining to the user associated with at least one other treatment device mode of the treatment device in addition to or instead of the first treatment device mode, wherein such use is, without limitation, to determine secondary conditions of the user.

In some embodiments, the systems and methods described herein may be configured to determine whether the at least one aspect of the at least one measurement pertaining to the user associated with the first treatment device mode of the treatment device is correlated with the at least one secondary condition, by writing to an associated memory the at least one aspect of the at least one measurement pertaining to the user associated with the first treatment device mode of the treatment device.

The associated memory may further be configured to be accessed by an artificial intelligence engine. The artificial intelligence engine may be configured to use at least one machine learning model to generate, using the at least one aspect of the at least one measurement pertaining to the user associated with the first treatment device mode of the treatment device, at least one of secondary condition output prediction. As used herein, a "secondary condition output prediction" refers to output generated by the machine learning model and/or the artificial intelligence engine. The artificial intelligence engine may include any suitable artificial intelligence engine, including those described herein. The at least one machine learning model may include any suitable machine learning model, including those described here. For example, the at least one machine learning model may include a deep network comprising multiple levels of non-linear operations or other suitable model.

In some embodiments, the artificial intelligence engine may be configured to use the at least one machine learning model to generate, further using secondary condition information associated with other users, the at least one of secondary condition output prediction. At least some of the other users may be associated with a cohort to which the user belongs; alternatively, all of the other users may be associated with the cohort of which the user belongs; further alternatively, the other users may be associated with other cohorts; or the other users may not be associated with cohorts. In some embodiments, the other users may have characteristics similar to those of the user. In some embodiments, measurements pertaining to the other users may include measurements similar to the at least one measurement pertaining to the user.

The at least one secondary condition output prediction generated by the at least one machine learning model may indicate one or more secondary conditions that may be associated with the patient. For example, the machine learning model may determine, based on the at least one aspect of the at least one measurement pertaining to the user associated with the first treatment device mode of the treatment device, that a predicted secondary condition may be affecting the patient. The at least one secondary condition output prediction may include a probabilistic prediction (using, for example and without limitation, parametric, non-parametric, Bayesian and/or Markovian probabilistic methods), a stochastic prediction (using, for example and without limitation, non-deterministic finite state automata), or a deterministic prediction (using, for example and without limitation, finite state automata). The systems and methods described herein may be configured to receive, from the artificial intelligence engine, the at least one secondary condition output prediction.

In some embodiments, the systems and methods described herein may be configured to, in response to a determination that the at least one aspect of the at least one measurement pertaining to the user associated with the first treatment device mode of the treatment device is correlated with the at least one at least one secondary condition of the user, generate secondary condition information indicating at least the secondary condition. The systems and methods described herein may be configured to write to an associated memory, for access at a computing device of a healthcare provider, the secondary condition information.

The systems and methods described herein may be configured to write to an associated memory, for access at the computing device of the healthcare provider and/or the user. The systems and methods may provide, at the computing device of the healthcare provider and/or the user, at least the at least one secondary condition output prediction. For example, the systems and methods describe herein may be configured to provide at least the at least one secondary condition output prediction to an interface configured to present at least the at least one secondary condition output prediction to the healthcare provider. The interface may include a graphical user interface configured to provide at least the at least one secondary condition output prediction and receive input from the healthcare provider. The interface may include one or more input fields, such as text input fields, dropdown selection input fields, radio button input fields, virtual switch input fields, virtual lever input fields, audio, haptic, tactile, biometric, gesture recognition, gesture control, touchless user interfaces (TUIs), kinetic user interfaces (KUIs), tangible user interfaces, wired gloves, depth-aware cameras, stereo cameras, gesture-based controllers, or otherwise activated and/or driven input fields, other suitable input fields, or a combination thereof.

In some embodiments, the healthcare provider may review at least the at least one secondary condition output prediction and determine whether to pursue treatment of one or more secondary conditions identified by the at least one secondary condition output prediction, to modify at least one aspect of the treatment plan, and/or to modify or adjust one or more characteristics of the treatment device.

In some embodiments, the systems and methods described herein may be configured to generate treatment information using the treatment data. The treatment information may include a summary of the performance, by the user while using the treatment device, of the treatment plan formatted, such that the treatment data is presentable at a computing device of a healthcare provider responsible for the performance of the treatment plan by the user. The treatment data may be presented to the user via the user's computing device, which may enable the user to better understand their progress, performance, and future goals. Further, presenting the treatment data to the user may motivate the user to continue to perform the treatment plan. In some embodiments, presenting the treatment data to the user may specify a problem of the treatment plan and/or non-compliance with the treatment plan, which may be subsequently addressed. The healthcare provider may include a medical professional (e.g., such as a doctor, a nurse, a therapist, and the like), an exercise professional (e.g., such as a coach, a trainer, a nutritionist, and the like), or another professional sharing at least one of medical and exercise attributes (e.g., such as an exercise physiologist, a physical therapist, an occupational therapist, and the like). As used herein, and without limiting the foregoing, a "healthcare provider" may be a human being, a robot, a virtual assistant, a virtual assistant in virtual and/or augmented reality, or an artificially intelligent entity, such entity including a software program, integrated software and hardware, or hardware alone.

The systems and methods described herein may be configured to write to an associated memory, for access at the computing device of the healthcare provider and/or the user. The systems and methods may provide, at the computing device of the healthcare provider and/or the user, the treatment information. For example, the systems and methods describe herein may be configured to provide the treatment information to an interface configured to present the treatment information to the healthcare provider. The interface may include a graphical user interface configured to provide the treatment information and to receive input from the healthcare provider. The interface may include one or more input fields, such as text input fields, dropdown selection input fields, radio button input fields, virtual switch input fields, virtual lever input fields, audio, haptic, tactile, biometric, or otherwise activated and/or driven input fields, other suitable input fields, or a combination thereof.

In some embodiments, the healthcare provider may review the treatment information and determine whether to modify at least one aspect of the treatment plan, and/or one or more characteristics of the treatment device. For example, the healthcare provider may review the treatment information and compare the treatment information to the treatment plan being performed by the user.

The healthcare provider may compare the following (i) expected information, which pertains to the user's expected or predicted performance when the user actually uses the treatment device to perform the treatment plan to (ii) the measurement information (e.g., indicated by the treatment information), which pertains to the user while the user is using the treatment device to perform the treatment plan.

The expected information may include one or more vital signs of the user, a respiration rate of the user, a heartrate of the user, a temperature of the user, a blood pressure of the user, other suitable information of the user, or a combination thereof. The healthcare provider may determine that the treatment plan is having the desired effect if one or more parts or portions of the measurement information are within an acceptable range associated with one or more corresponding parts or portions of the expected information. Alternatively, the healthcare provider may determine that the treatment plan is not having the desired effect (e.g., not achieving the desired effect or a portion of the desired effect) if one or more parts or portions of the measurement information are outside of the range associated with one or more corresponding parts or portions of the expected information.

For example, the healthcare provider may determine whether a blood pressure value (e.g., systolic pressure, diastolic pressure, and/or pulse pressure) corresponding to the user while the user uses the treatment device (e.g., indicated by the measurement information) is within an acceptable range (e.g., plus or minus 1%, plus or minus 5%, plus or minus a particular number of units suitable for the measurement (e.g., actual or digitally equivalent column inches of mercury for blood pressure, and the like), or any suitable range) of an expected blood pressure value indicated by the expected information. The healthcare provider may determine that the treatment plan is having the desired effect (e.g., achieving the desired effect or a portion of the desired effect) if the blood pressure value corresponding to the user while the user uses the treatment device is within the range of the expected blood pressure value. Alternatively, the healthcare provider may determine that the treatment plan is not having the desired effect if the blood pressure value corresponding to the user while the user uses the treatment device is outside of the range of the expected blood pressure value.

In some embodiments, the healthcare provider may compare the expected characteristics of the treatment device while the user uses the treatment device to perform the treatment plan with characteristics of the treatment device indicated by the treatment information. For example, the healthcare provider may compare an expected resistance setting of the treatment device with an actual resistance setting of the treatment device indicated by the treatment information. The healthcare provider may determine that the user is performing the treatment plan properly if the actual characteristics of the treatment device indicated by the treatment information are within a range of corresponding ones of the expected characteristics of the treatment device. Alternatively, the healthcare provider may determine that the user is not performing the treatment plan properly if the actual characteristics of the treatment device indicated by the treatment information are outside the range of corresponding ones of the expected characteristics of the treatment device.

If the healthcare provider determines that the treatment information indicates that the user is performing the treatment plan properly and/or that the treatment plan is having the desired effect, the healthcare provider may determine not to modify the at least one aspect of the treatment plan, and/or the one or more characteristics of the treatment device. Alternatively, while the user uses the treatment device to perform the treatment plan, if the healthcare provider determines that the treatment information indicates that the user is not or has not been performing the treatment plan properly and/or that the treatment plan is not or has not been having the desired effect, the healthcare provider may determine to modify the at least one aspect of the treatment plan and/or the one or more characteristics of the treatment device.

In some embodiments, the healthcare provider may interact with the interface to provide treatment plan input indicating one or more modifications to the treatment plan, and/or one or more characteristics of the treatment device if the healthcare provider determines to modify the treatment plan, and/or to one or more characteristics of the treatment device. For example, the healthcare provider may use the interface to provide input indicating an increase or decrease in the resistance setting of the treatment device, or other suitable modification to the one or more characteristics of the treatment device. Additionally, or alternatively, the healthcare provider may use the interface to provide input indicating a modification to the treatment plan. For example, the healthcare provider may use the interface to provide input indicating an increase or decrease in an amount of time the user is required to use the treatment device according to the treatment plan, or other suitable modifications to the treatment plan.

In some embodiments, the systems and methods described herein may be configured to modify the treatment plan based on one or more modifications indicated by the treatment plan input. Additionally, or alternatively, the systems and methods described herein may be configured to modify the one or more characteristics of the treatment device based on the modified treatment plan and/or the treatment plan input. For example, the treatment plan input may indicate that the one or more characteristics of the treatment device should be modified and/or the modified treatment plan may require or indicate adjustments to the treatment device in order for the user to achieve the desired results of the modified treatment plan.

In some embodiments, while the user uses the treatment device to perform the modified treatment plan, the systems and methods described herein may be configured to receive the subsequent treatment data pertaining to the user. For example, after the healthcare provider provides input modifying the treatment plan and/or controlling the one or more characteristics of the treatment device, the user may continue using the treatment device to perform the modified treatment plan. The subsequent treatment data may correspond to treatment data generated while the user uses the treatment device to perform the modified treatment plan. In some embodiments, the subsequent treatment data may correspond to treatment data generated while the user continues to use the treatment device to perform the treatment plan, after the healthcare provider has received the treatment information and determined not to modify the treatment plan and/or control the one or more characteristics of the treatment device.

Based on subsequent treatment plan input received from the computing device of the healthcare provider, the systems and methods described herein may be configured to further modify the treatment plan, and/or to further control the one or more characteristics of the treatment device. The subsequent treatment plan input may correspond to input provided by the healthcare provider, at the interface, in response to receiving and/or reviewing subsequent treatment information corresponding to the subsequent treatment data. It should be understood that the systems and methods described herein may be configured to continuously and/or periodically provide treatment information to the computing device of the healthcare provider based on treatment data continuously and/or periodically received from the sensors or other suitable sources described herein.

The healthcare provider may receive and/or review treatment information continuously or periodically while the user uses the treatment device to perform the treatment plan. Based on one or more trends indicated by the continuously and/or periodically received treatment information, the healthcare provider may determine whether to modify the treatment plan, and/or to control the one or more characteristics of the treatment device. For example, the one or more trends may indicate an increase in heartrate or other suitable trends indicating that the user is not performing the treatment plan properly and/or that performance of the treatment plan by the user is not having the desired effect.

In some embodiments, during an adaptive telemedicine session, the systems and methods described herein may be configured to use artificial intelligence and/or machine learning to assign patients to cohorts and to dynamically control a treatment device based on the assignment. The term "adaptive telemedicine" may refer to a telemedicine session that is dynamically adapted based on one or more factors, criteria, parameters, characteristics, or the like. The one or more factors, criteria, parameters, characteristics, or the like may pertain to the user (e.g., heartrate, blood pressure, perspiration rate, pain level, or the like), the treatment device (e.g., pressure, range of motion, speed of motor, etc.), details of the treatment plan, and so forth.

In some embodiments, numerous patients may be prescribed numerous treatment devices because the numerous patients are recovering from the same medical procedure and/or suffering from the same injury. The numerous treatment devices may be provided to the numerous patients. The treatment devices may be used by the patients to perform treatment plans in their residences, at gyms, at rehabilitative centers, at hospitals, or at any suitable locations, including permanent or temporary domiciles.

In some embodiments, the treatment devices may be communicatively coupled to a server. Characteristics of the patients, including the treatment data, may be collected before, during, and/or after the patients perform the treatment plans. For example, any or each of the personal information, the performance information, and the measurement information may be collected before, during, and/or after a patient performs the treatment plans. The results (e.g., improved performance or decreased performance) of performing each exercise may be collected from the treatment device throughout the treatment plan and after the treatment plan is performed. The parameters, settings, configurations, etc. (e.g., position of pedal, amount of resistance, etc.) of the treatment device may be collected before, during, and/or after the treatment plan is performed.

Each characteristic of the patient, each result, and each parameter, setting, configuration, etc. may be timestamped and may be correlated with a particular step or set of steps in the treatment plan. Such a technique may enable the determination of which steps in the treatment plan lead to desired results (e.g., improved muscle strength, range of motion, etc.) and which steps lead to diminishing returns (e.g., continuing to exercise after 3 minutes actually delays or harms recovery).

Data may be collected from the treatment devices and/or any suitable computing device (e.g., computing devices where personal information is entered, such as the interface of the computing device described herein, a clinician interface, patient interface, and the like) over time as the patients use the treatment devices to perform the various treatment plans. The data that may be collected may include the characteristics of the patients, the treatment plans performed by the patients, the results of the treatment plans, any of the data described herein, any other suitable data, or a combination thereof.

In some embodiments, the data may be processed to group certain people into cohorts. The people may be grouped by people having certain or selected similar characteristics, treatment plans, and results of performing the treatment plans. For example, athletic people having no medical conditions who perform a treatment plan (e.g., use the treatment device for 30 minutes a day 5 times a week for 3 weeks) and who fully recover may be grouped into a first cohort. Older people who are classified obese and who perform a treatment plan (e.g., use the treatment plan for 10 minutes a day 3 times a week for 4 weeks) and who improve their range of motion by 75 percent may be grouped into a second cohort.

In some embodiments, an artificial intelligence engine may include one or more machine learning models that are trained using the cohorts. In some embodiments, the artificial intelligence engine may be used to identify trends and/or patterns and to define new cohorts based on achieving desired results from the treatment plans and machine learning models associated therewith may be trained to identify such trends and/or patterns and to recommend and rank the desirability of the new cohorts. For example, the one or more machine learning models may be trained to receive an input of characteristics of a new patient and to output a treatment plan for the patient that results in a desired result. The machine learning models may match a pattern between the characteristics of the new patient and at least one patient of the patients included in a particular cohort. When a pattern is matched, the machine learning models may assign the new patient to the particular cohort and select the treatment plan associated with the at least one patient. The artificial intelligence engine may be configured to control, distally and based on the treatment plan, the treatment device while the new patient uses the treatment device to perform the treatment plan.

As may be appreciated, the characteristics of the new patient (e.g., a new user) may change as the new patient uses the treatment device to perform the treatment plan. For example, the performance of the patient may improve quicker than expected for people in the cohort to which the new patient is currently assigned. Accordingly, the machine learning models may be trained to dynamically reassign, based on the changed characteristics, the new patient to a different cohort that includes people having characteristics similar to the now-changed characteristics as the new patient. For example, a clinically obese patient may lose weight and no longer meet the weight criterion for the initial cohort, result in the patient's being reassigned to a different cohort with a different weight criterion.

A different treatment plan may be selected for the new patient, and the treatment device may be controlled, distally (e.g., which may be referred to as remotely) and based on the different treatment plan, while the new patient uses the treatment device to perform the treatment plan. Such techniques may provide the technical solution of distally controlling a treatment device.

Further, the systems and methods described herein may lead to faster recovery times and/or better results for the patients because the treatment plan that most accurately fits their characteristics is selected and implemented, in real-time, at any given moment. "Real-time" may also refer to near real-time, which may be less than 10 seconds. As described herein, the term "results" may refer to medical results or medical outcomes. Results and outcomes may refer to responses to medical actions.

Depending on what result is desired, the artificial intelligence engine may be trained to output several treatment plans. For example, one result may include recovering to a threshold level (e.g., 75% range of motion) in a fastest amount of time, while another result may include fully recovering (e.g., 100% range of motion) regardless of the amount of time. The data obtained from the patients and sorted into cohorts may indicate that a first treatment plan provides the first result for people with characteristics similar to the patient's, and that a second treatment plan provides the second result for people with characteristics similar to the patient.

Further, the artificial intelligence engine may be trained to output treatment plans that are not optimal i.e., sub-optimal, nonstandard, or otherwise excluded (all referred to, without limitation, as "excluded treatment plans") for the patient. For example, if a patient has high blood pressure, a particular exercise may not be approved or suitable for the patient as it may put the patient at unnecessary risk or even induce a hypertensive crisis and, accordingly, that exercise may be flagged in the excluded treatment plan for the patient. In some embodiments, the artificial intelligence engine may monitor the treatment data received while the patient (e.g., the user) with, for example, high blood pressure, uses the treatment device to perform an appropriate treatment plan and may modify the appropriate treatment plan to include features of an excluded treatment plan that may provide beneficial results for the patient if the treatment data indicates the patient is handling the appropriate treatment plan without aggravating, for example, the high blood pressure condition of the patient. In some embodiments, the artificial intelligence engine may modify the treatment plan if the monitored data shows the plan to be inappropriate or counterproductive for the user.

In some embodiments, the treatment plans and/or excluded treatment plans may be presented, during a telemedicine or telehealth session, to a healthcare provider. The healthcare provider may select a particular treatment plan for the patient to cause that treatment plan to be transmitted to the patient and/or to control, based on the treatment plan, the treatment device. In some embodiments, to facilitate telehealth or telemedicine applications, including remote diagnoses, determination of treatment plans and rehabilitative and/or pharmacologic prescriptions, the artificial intelligence engine may receive and/or operate distally from the patient and the treatment device.

In such cases, the recommended treatment plans and/or excluded treatment plans may be presented simultaneously with a video of the patient in real-time or near real-time during a telemedicine or telehealth session on a user interface of a computing device of a healthcare provider. The video may also be accompanied by audio, text and other multimedia information. Real-time may refer to less than or equal to 2 seconds. Real-time may also refer to near real-time, which may be less than 10 seconds or any reasonably proximate difference between two different times. Additionally, or alternatively, near real-time may refer to any interaction of a sufficiently short time to enable two individuals to engage in a dialogue via such user interface and will generally be less than 10 seconds but greater than 2 seconds.

Presenting the treatment plans generated by the artificial intelligence engine concurrently with a presentation of the patient video may provide an enhanced user interface because the healthcare provider may continue to visually and/or otherwise communicate with the patient while also reviewing the treatment plans on the same user interface. The enhanced user interface may improve the healthcare provider's experience using the computing device and may encourage the healthcare provider to reuse the user interface. Such a technique may also reduce computing resources (e.g., processing, memory, network) because the healthcare provider does not have to switch to another user interface screen to enter a query for a treatment plan to recommend based on the characteristics of the patient. The artificial intelligence engine may be configured to provide, dynamically on the fly, the treatment plans and excluded treatment plans.

In some embodiments, the treatment device may be adaptive and/or personalized because its properties, configurations, and positions may be adapted to the needs of a particular patient. For example, the pedals may be dynamically adjusted on the fly (e.g., via a telemedicine session or based on programmed configurations in response to certain measurements being detected) to increase or decrease a range of motion to comply with a treatment plan designed for the user. In some embodiments, a healthcare provider may adapt, remotely during a telemedicine session, the treatment device to the needs of the patient by causing a control instruction to be transmitted from a server to treatment device. Such adaptive nature may improve the results of recovery for a patient, furthering the goals of personalized medicine, and enabling personalization of the treatment plan on a per-individual basis.

A technical problem may occur which relates to the information pertaining to the patient's medical condition being received in disparate formats. For example, a server may receive the information pertaining to a medical condition of the patient from one or more sources (e.g., from an electronic medical record (EMR) system, application programming interface (API), or any suitable system that has information pertaining to the medical condition of the patient). That is, some sources used by various healthcare providers may be installed on their local computing devices and may use proprietary formats. Accordingly, some embodiments of the present disclosure may use an API to obtain, via interfaces exposed by APIs used by the sources, the formats used by the sources. In some embodiments, when information is received from the sources, the API may map, translate and/or convert the format used by the sources to a standardized format used by the artificial intelligence engine. Further, the information mapped, translated and/or converted to the standardized format used by the artificial intelligence engine may be stored in a database accessed by the artificial intelligence engine when performing any of the techniques disclosed herein. Using the information mapped, translated and/or converted to a standardized format may enable the more accurate determination of the procedures to perform for the patient and/or a billing sequence.

To that end, the standardized information may enable the generation of treatment plans and/or billing sequences having a particular format configured to be processed by various applications (e.g., telehealth). For example, applications, such as telehealth applications, may be executing on various computing devices of medical professionals and/or patients. The applications (e.g., standalone or web-based) may be provided by a server and may be configured to process data according to a format in which the treatment plans are implemented. Accordingly, the disclosed embodiments may provide a technical solution by (i) receiving, from various sources (e.g., EMR systems), information in non-standardized and/or different formats; (ii) standardizing the information; and (iii) generating, based on the standardized information, treatment plans having standardized formats capable of being processed by applications (e.g., telehealth applications) executing on computing devices of medical professional and/or patients.

FIG. 1 generally illustrates a block diagram of a computer-implemented system 10, hereinafter called "the system" for managing a treatment plan. Managing the treatment plan may include using an artificial intelligence engine to recommend treatment plans and/or provide excluded treatment plans that should not be recommended to a patient.

The system 10 also includes a server 30 configured to store (e.g., write to an associated memory) and to provide data related to managing the treatment plan. The server 30 may include one or more computers and may take the form of a distributed and/or virtualized computer or computers. The server 30 also includes a first communication interface 32 configured to communicate with the clinician interface 20 via a first network 34. In some embodiments, the first network 34 may include wired and/or wireless network connections such as Wi-Fi, Bluetooth, ZigBee, Near-Field Communications (NFC), cellular data network, etc. The server 30 includes a first processor 36 and a first machine-readable storage memory 38, which may be called a "memory" for short, holding first instructions 40 for performing the various actions of the server 30 for execution by the first processor 36.

The server 30 is configured to store data regarding the treatment plan. For example, the memory 38 includes a system data store 42 configured to hold system data, such as data pertaining to treatment plans for treating one or more patients. The server 30 is also configured to store data regarding performance by a patient in following a treatment plan. For example, the memory 38 includes a patient data store 44 configured to hold patient data, such as data pertaining to the one or more patients, including data representing each patient's performance within the treatment plan.

Additionally, or alternatively, the characteristics (e.g., personal, performance, measurement, etc.) of the people, the treatment plans followed by the people, the level of compliance with the treatment plans, and the results of the treatment plans may use correlations and other statistical or probabilistic measures to enable the partitioning of or to partition the treatment plans into different patient cohort-equivalent databases in the patient data store 44. For example, the data for a first cohort of first patients having a first similar injury, a first similar medical condition, a first similar medical procedure performed, a first treatment plan followed by the first patient, and a first result of the treatment plan may be stored in a first patient database. The data for a second cohort of second patients having a second similar injury, a second similar medical condition, a second similar medical procedure performed, a second treatment plan followed by the second patient, and a second result of the treatment plan may be stored in a second patient database. Any single characteristic or any combination of characteristics may be used to separate the cohorts of patients. In some embodiments, the different cohorts of patients may be stored in different partitions or volumes of the same database. There is no specific limit to the number of different cohorts of patients allowed, other than as limited by mathematical combinatoric and/or partition theory.

This characteristic data, treatment plan data, and results data may be obtained from numerous treatment devices and/or computing devices and/or digital storage media over time and stored in the data store 44. The characteristic data, treatment plan data, and results data may be correlated in the patient-cohort databases in the patient data store 44. The characteristics of the people may include personal information, performance information, and/or measurement information.

In addition to the historical information about other people stored in the patient cohort-equivalent databases, real-time or near-real-time information based on the current patient's characteristics about a current patient being treated may be stored in an appropriate patient cohort-equivalent database. The characteristics of the patient may be determined to match or be similar to the characteristics of another person in a particular cohort (e.g., cohort A) and the patient may be assigned to that cohort.

In some embodiments, the server 30 may execute an artificial intelligence (AI) engine 11 that uses one or more machine learning models 13 to perform at least one of the embodiments disclosed herein. The server 30 may include a training engine 9 capable of generating the one or more machine learning models 13. The machine learning models 13 may be trained to assign people to certain cohorts based on their characteristics, select treatment plans using real-time and historical data correlations involving patient cohort-equivalents, and control a treatment device 70, among other things.

The one or more machine learning models 13 may be generated by the training engine 9 and may be implemented in computer instructions executable by one or more processing devices of the training engine 9 and/or the servers 30. To generate the one or more machine learning models 13, the training engine 9 may train the one or more machine learning models 13. The one or more machine learning models 13 may be used by the artificial intelligence engine 11.

The training engine 9 may be a rackmount server, a router computer, a personal computer, a portable digital assistant, a smartphone, a laptop computer, a tablet computer, a netbook, a desktop computer, an Internet of Things (IoT) device, any other suitable computing device, or a combination thereof. The training engine 9 may be cloud-based or a real-time software platform, and it may include privacy software or protocols, and/or security software or protocols.

To train the one or more machine learning models 13, the training engine 9 may use a training data set of a corpus of the characteristics of the people that used the treatment device 70 to perform treatment plans, the details (e.g., treatment protocol including exercises, amount of time to perform the exercises, how often to perform the exercises, a schedule of exercises, parameters/configurations/settings of the treatment device 70 throughout each step of the treatment plan, etc.) of the treatment plans performed by the people using the treatment device 70, and the results of the treatment plans performed by the people. The one or more machine learning models 13 may be trained to match patterns of characteristics of a patient with characteristics of other people assigned to a particular cohort. The term "match" may refer to an exact match, a correlative match, a substantial match, etc. The one or more machine learning models 13 may be trained to receive the characteristics of a patient as input, map the characteristics to characteristics of people assigned to a cohort, and select a treatment plan from that cohort. The one or more machine learning models 13 may also be trained to control, based on the treatment plan, the treatment device 70. The one or more machine learning models 13 may also be trained to provide one or more treatment plans options to a healthcare provider to select from to control the treatment device 70.

Different machine learning models 13 may be trained to recommend different treatment plans for different desired results. For example, one machine learning model may be trained to recommend treatment plans for most effective recovery, while another machine learning model may be trained to recommend treatment plans based on speed of recovery.

Using training data that includes training inputs and corresponding target outputs, the one or more machine learning models 13 may refer to model artifacts created by the training engine 9. The training engine 9 may find patterns in the training data wherein such patterns map the training input to the target output and generate the machine learning models 13 that capture these patterns. In some embodiments, the artificial intelligence engine 11, the database 33, and/or the training engine 9 may reside on another component (e.g., assistant interface 94, clinician interface 20, etc.) depicted in FIG. 1.

The one or more machine learning models 13 may comprise, e.g., a single level of linear or non-linear operations (e.g., a support vector machine [SVM]) or the machine learning models 13 may be a deep network, i.e., a machine learning model comprising multiple levels of non-linear operations. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

The system 10 also includes a patient interface 50 configured to communicate information to a patient and to receive feedback from the patient. Specifically, the patient interface includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various different visual, audio, or other presentation technologies. For example, the output device 54 may include a non-visual display, such as an audio signal, which may include spoken language and/or other sounds such as tones, chimes, and/or melodies, which may signal different conditions and/or directions. The output device 54 may comprise one or more different display screens presenting various data and/or interfaces or controls for use by the patient. The output device 54 may include graphics, which may be presented by a web-based interface and/or by a computer program or application (App.). In some embodiments, the patient interface 50 may include functionality provided by or similar to existing voice-based assistants such as Siri by Apple, Alexa by Amazon, Google Assistant, or Bixby by Samsung.

As is generally illustrated in FIG. 1, the patient interface 50 includes a second communication interface 56, which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data network, etc. In some embodiments, the second network 58 may be the same as and/or operationally coupled to the first network 34.

The patient interface 50 includes a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 may include wired and/or wireless communications. In some embodiments, the local communication interface 68 may include a local wireless network such as Wi-Fi, Bluetooth, ZigBee, Near-Field Communications (NFC), cellular data network, etc.

The system 10 also includes a treatment device 70 configured to be manipulated by the patient and/or to manipulate a body part of the patient for performing activities according to the treatment plan. In some embodiments, the treatment device 70 may take the form of an exercise and rehabilitation apparatus configured to perform and/or to aid in the performance of a rehabilitation regimen, which may be an orthopedic rehabilitation regimen, and the treatment includes rehabilitation of a body part of the patient, such as a joint or a bone or a muscle group. The treatment device 70 may be any suitable medical, rehabilitative, therapeutic, etc. apparatus configured to be controlled distally via another computing device to treat a patient and/or exercise the patient. The treatment device 70 may be an electromechanical machine including one or more weights, an electromechanical bicycle, an electromechanical spin-wheel, a smart-mirror, a treadmill, an interactive environment system, or the like. The body part may include, for example, a spine, a hand, a foot, a knee, or a shoulder. The body part may include a part of a joint, a bone, or a muscle group, such as one or more vertebrae, a tendon, or a ligament. As is generally illustrated in FIG. 1, the treatment device 70 includes a controller 72, which may include one or more processors, computer memory, and/or other components. The treatment device 70 also includes a fourth communication interface 74 configured to communicate with the patient interface 50 via the local communication interface 68. The treatment device 70 also includes one or more internal sensors 76 and an actuator 78, such as a motor. The actuator 78 may be used, for example, for moving the patient's body part and/or for resisting forces by the patient.

The internal sensors 76 may measure one or more operating characteristics of the treatment device 70 such as, for example, a force, a position, a speed, and/or a velocity. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the treatment device 70, where such distance may correspond to a range of motion that the patient's body part is able to achieve. In some embodiments, the internal sensors 76 may include a force sensor configured to measure a force applied by the patient. For example, an internal sensor 76 in the form of a force sensor may measure a force or weight the patient is able to apply, using a particular body part, to the treatment device 70.

The system 10 generally illustrated in FIG. 1 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone.

The system 10 generally illustrated in FIG. 1 also includes a goniometer 84, which communicates with the server 30 via the local communication interface 68 of the patient interface 50. The goniometer 84 measures an angle of the patient's body part. For example, the goniometer 84 may measure the angle of flex of a patient's knee or elbow or shoulder.

The system 10 generally illustrated in FIG. 1 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's foot when pedaling a stationary bike.

The system 10 generally illustrated in FIG. 1 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a person having responsibility for the treatment plan, such as an orthopedic surgeon.

The system 10 generally illustrated in FIG. 1 also includes a reporting interface 92 which may be similar or identical to the clinician interface 20. In some embodiments, the reporting interface 92 may have less functionality from what is provided on the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display patient identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different patients.

The system 10 includes an assistant interface 94 for a healthcare provider, such as those described herein, to remotely communicate with the patient interface 50 and/or the treatment device 70. Such remote communications may enable the healthcare provider to provide assistance or guidance to a patient using the system 10. More specifically, the assistant interface 94 is configured to communicate a telemedicine signal 96, 97, 98a, 98b, 99a, 99b with the patient interface 50 via a network connection such as, for example, via the first network 34 and/or the second network 58.

The telemedicine signal 96, 97, 98a, 98b, 99a, 99b comprises one of an audio signal 96, an audiovisual signal 97, an interface control signal 98a for controlling a function of the patient interface 50, an interface monitor signal 98b for monitoring a status of the patient interface 50, an apparatus control signal 99a for changing an operating parameter of the treatment device 70, and/or an apparatus monitor signal 99b for monitoring a status of the treatment device 70. In some embodiments, each of the control signals 98a, 99a may be unidirectional, conveying commands from the assistant interface 94 to the patient interface 50. In some embodiments, in response to successfully receiving a control signal 98a, 99a and/or to communicate successful and/or unsuccessful implementation of the requested control action, an acknowledgement message may be sent from the patient interface 50 to the assistant interface 94.

In some embodiments, each of the monitor signals 98b, 99b may be unidirectional, status-information commands from the patient interface 50 to the assistant interface 94. In some embodiments, an acknowledgement message may be sent from the assistant interface 94 to the patient interface 50 in response to successfully receiving one of the monitor signals 98b, 99b.

In some embodiments, the patient interface 50 may be configured as a pass-through for the apparatus control signals 99a and the apparatus monitor signals 99b between the treatment device 70 and one or more other devices, such as the assistant interface 94 and/or the server 30. For example, the patient interface 50 may be configured to transmit an apparatus control signal 99a in response to an apparatus control signal 99a within the telemedicine signal 96, 97, 98a, 98b, 99a, 99b from the assistant interface 94.

In some embodiments, the assistant interface 94 may be presented on a shared physical device as the clinician interface 20. For example, the clinician interface 20 may include one or more screens that implement the assistant interface 94. Alternatively or additionally, the clinician interface 20 may include additional hardware components, such as a video camera, a speaker, and/or a microphone, to implement aspects of the assistant interface 94.

In some embodiments, one or more portions of the telemedicine signal 96, 97, 98a, 98b, 99a, 99b may be generated from a prerecorded source (e.g., an audio recording, a video recording, or an animation) for presentation by the output device 54 of the patient interface 50. For example, a tutorial video may be streamed from the server 30 and presented upon the patient interface 50. Content from the prerecorded source may be requested by the patient via the patient interface 50. Alternatively, via a control on the assistant interface 94, the healthcare provider may cause content from the prerecorded source to be played on the patient interface 50.

The assistant interface 94 includes an assistant input device 22 and an assistant display 24, which may be collectively called an assistant user interface 22, 24. The assistant input device 22 may include one or more of a telephone, a keyboard, a mouse, a trackpad, or a touch screen, for example. Alternatively or additionally, the assistant input device 22 may include one or more microphones. In some embodiments, the one or more microphones may take the form of a telephone handset, headset, or wide-area microphone or microphones configured for the healthcare provider to speak to a patient via the patient interface 50.

In some embodiments, assistant input device 22 may be configured to provide voice-based functionalities, with hardware and/or software configured to interpret spoken instructions by the healthcare provider by using the one or more microphones. The assistant input device 22 may include functionality provided by or similar to existing voice-based assistants such as Siri by Apple, Alexa by Amazon, Google Assistant, or Bixby by Samsung. The assistant input device 22 may include other hardware and/or software components. The assistant input device 22 may include one or more general purpose devices and/or special-purpose devices.

The assistant display 24 may take one or more different forms including, for example, a computer monitor or display screen on a tablet, a smartphone, or a smart watch. The assistant display 24 may include other hardware and/or software components such as projectors, virtual reality capabilities, or augmented reality capabilities, etc. The assistant display 24 may incorporate various different visual, audio, or other presentation technologies. For example, the assistant display 24 may include a non-visual display, such as an audio signal, which may include spoken language and/or other sounds such as tones, chimes, melodies, and/or compositions, which may signal different conditions and/or directions. The assistant display 24 may comprise one or more different display screens presenting various data and/or interfaces or controls for use by the healthcare provider. The assistant display 24 may include graphics, which may be presented by a web-based interface and/or by a computer program or application (App.).

In some embodiments, the system 10 may provide computer translation of language from the assistant interface 94 to the patient interface 50 and/or vice-versa. The computer translation of language may include computer translation of spoken language and/or computer translation of text. Additionally or alternatively, the system 10 may provide voice recognition and/or spoken pronunciation of text. For example, the system 10 may convert spoken words to printed text and/or the system 10 may audibly speak language from printed text. The system 10 may be configured to recognize spoken words by any or all of the patient, the clinician, and/or the healthcare provider. In some embodiments, the system 10 may be configured to recognize and react to spoken requests or commands by the patient. For example, in response to a verbal command by the patient (which may be given in any one of several different languages), the system 10 may automatically initiate a telemedicine session.

In some embodiments, the server 30 may generate aspects of the assistant display 24 for presentation by the assistant interface 94. For example, the server 30 may include a web server configured to generate the display screens for presentation upon the assistant display 24. For example, the artificial intelligence engine 11 may generate recommended treatment plans and/or excluded treatment plans for patients and generate the display screens including those recommended treatment plans and/or external treatment plans for presentation on the assistant display 24 of the assistant interface 94. In some embodiments, the assistant display 24 may be configured to present a virtualized desktop hosted by the server 30. In some embodiments, the server 30 may be configured to communicate with the assistant interface 94 via the first network 34. In some embodiments, the first network 34 may include a local area network (LAN), such as an Ethernet network.

In some embodiments, the first network 34 may include the Internet, and communications between the server 30 and the assistant interface 94 may be secured via privacy enhancing technologies, such as, for example, by using encryption over a virtual private network (VPN). Alternatively or additionally, the server 30 may be configured to communicate with the assistant interface 94 via one or more networks independent of the first network 34 and/or other communication means, such as a direct wired or wireless communication channel. In some embodiments, the patient interface 50 and the treatment device 70 may each operate from a patient location geographically separate from a location of the assistant interface 94. For example, the patient interface 50 and the treatment device 70 may be used as part of an in-home rehabilitation system, which may be aided remotely by using the assistant interface 94 at a centralized location, such as a clinic or a call center.

In some embodiments, the assistant interface 94 may be one of several different terminals (e.g., computing devices) that may be grouped together, for example, in one or more call centers or at one or more clinicians' offices. In some embodiments, a plurality of assistant interfaces 94 may be distributed geographically. In some embodiments, a person may work as a healthcare provider remotely from any conventional office infrastructure. Such remote work may be performed, for example, where the assistant interface 94 takes the form of a computer and/or telephone. This remote work functionality may allow for work-from-home arrangements that may include part time and/or flexible work hours for a healthcare provider.

Figure 2:
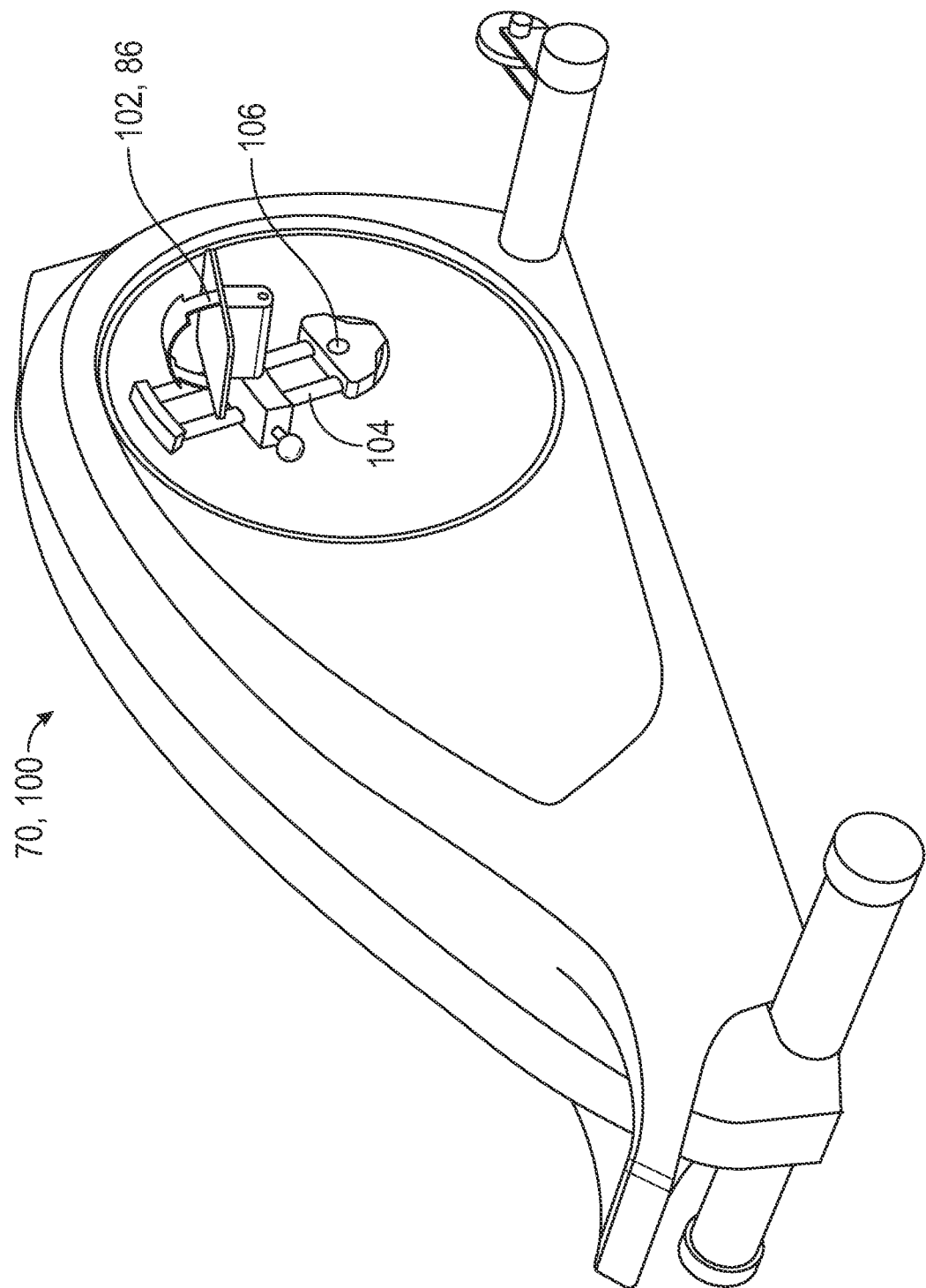
FIG. 2 generally illustrates a perspective view of an embodiment of a treatment device according to the principles of the present disclosure.
Figure 3:
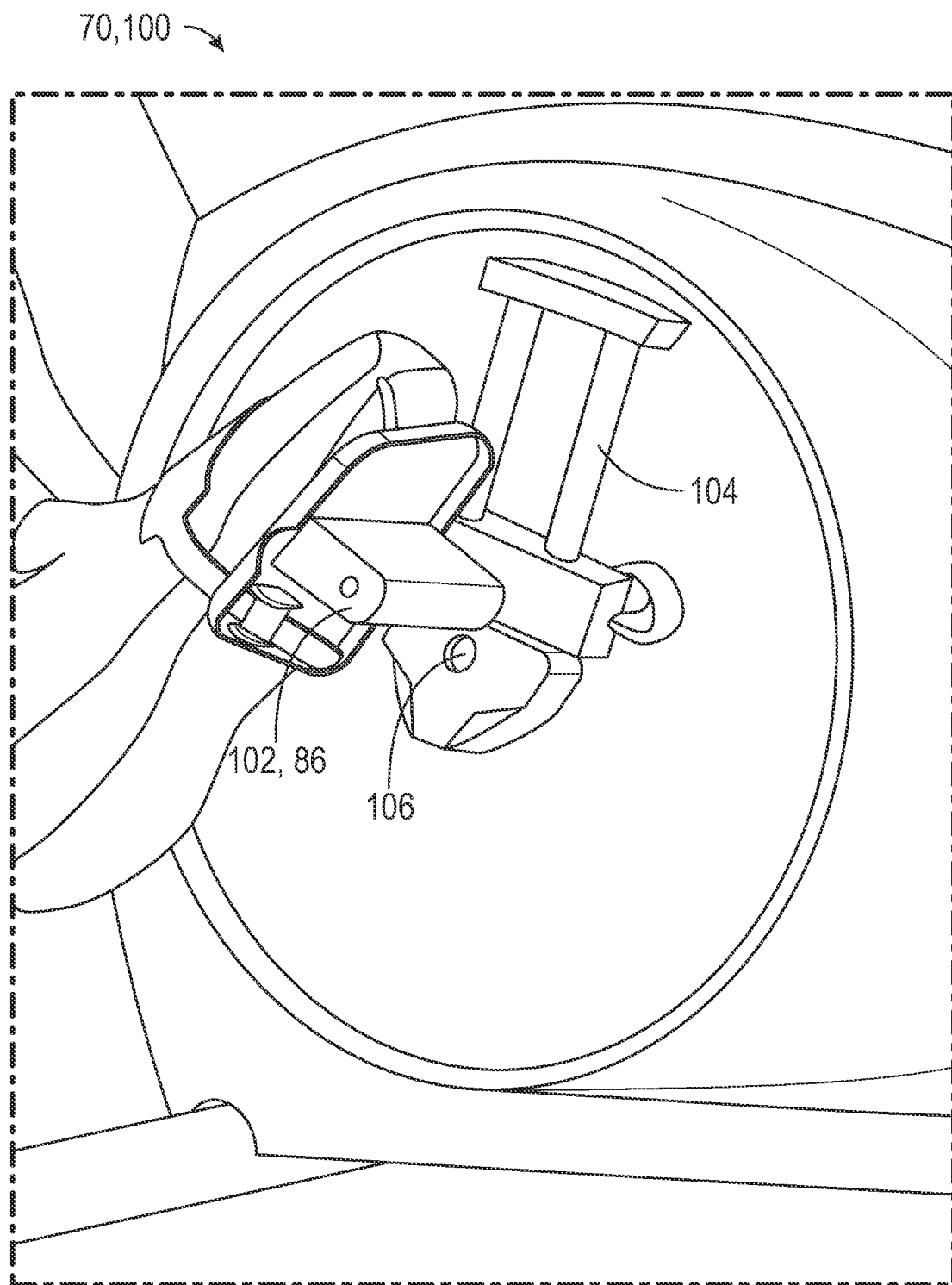
FIG. 3 generally illustrates a perspective view of a pedal of the treatment device of FIG. 2 according to the principles of the present disclosure.

FIGS. 2-3 show an embodiment of a treatment device 70. More specifically, FIG. 2 generally illustrates a treatment device 70 in the form of a stationary cycling machine 100, which may be called a stationary bike, for short. The stationary cycling machine 100 includes a set of pedals 102 each attached to a pedal arm 104 for rotation about an axle 106. In some embodiments, and as is generally illustrated in FIG. 2, the pedals 102 are movable on the pedal arms 104 in order to adjust a range of motion used by the patient in pedaling. For example, the pedals being located inwardly toward the axle 106 corresponds to a smaller range of motion than when the pedals are located outwardly away from the axle 106. One or more pressure sensors 86 is attached to or embedded within one or both of the pedals 102 for measuring an amount of force applied by the patient on a pedal 102. The pressure sensor 86 may communicate wirelessly to the treatment device 70 and/or to the patient interface 50.

Figure 4:
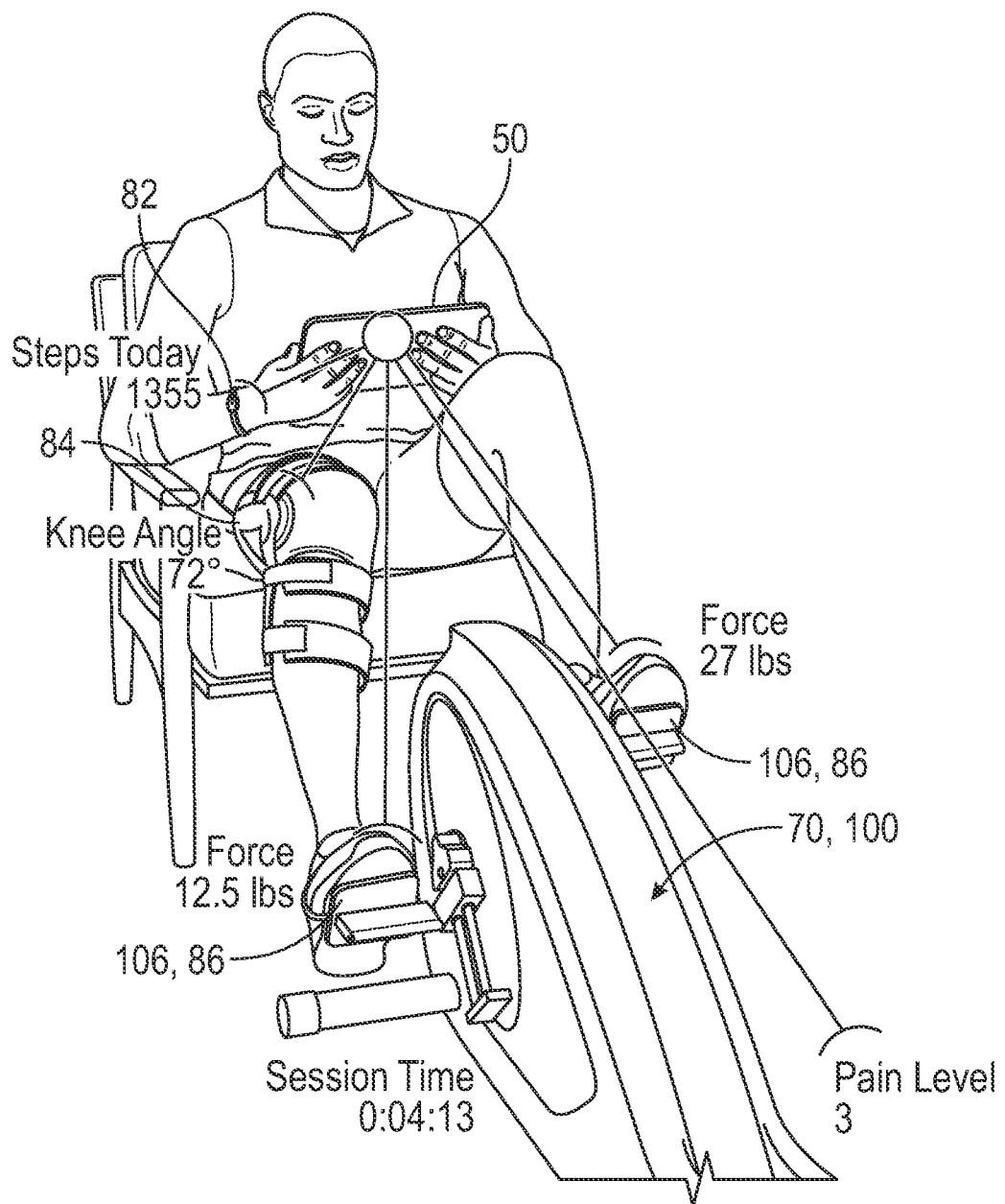
FIG. 4 generally illustrates a perspective view of a person using the treatment device of FIG. 2 according to the principles of the present disclosure.

FIG. 4 generally illustrates a person (a patient) using the treatment device of FIG. 2 and showing sensors and various data parameters connected to a patient interface 50. The example patient interface 50 is a tablet computer or smartphone, or a phablet, such as an iPad, an iPhone, an Android device, or a Surface tablet, which is held manually by the patient. In some other embodiments, the patient interface 50 may be embedded within or attached to the treatment device 70.

FIG. 4 generally illustrates the patient wearing the ambulation sensor 82 on his wrist, with a note showing "STEPS TODAY 1355", indicating that the ambulation sensor 82 has recorded and transmitted that step count to the patient interface 50. FIG. 4 also generally illustrates the patient wearing the goniometer 84 on his right knee, with a note showing "KNEE ANGLE 72°", indicating that the goniometer 84 is measuring and transmitting that knee angle to the patient interface 50. FIG. 4 also generally illustrates a right side of one of the pedals 102 with a pressure sensor 86 showing "FORCE 12.5 lbs.," indicating that the right pedal pressure sensor 86 is measuring and transmitting that force measurement to the patient interface 50.

FIG. 4 also generally illustrates a left side of one of the pedals 102 with a pressure sensor 86 showing "FORCE 27 lbs.", indicating that the left pedal pressure sensor 86 is measuring and transmitting that force measurement to the patient interface 50. FIG. 4 also generally illustrates other patient data, such as an indicator of "SESSION TIME 0:04:13", indicating that the patient has been using the treatment device 70 for 4 minutes and 13 seconds. This session time may be determined by the patient interface 50 based on information received from the treatment device 70. FIG. 4 also generally illustrates an indicator showing "PAIN LEVEL 3". Such a pain level may be obtained from the patent in response to a solicitation, such as a question, presented upon the patient interface 50.

Figure 5:
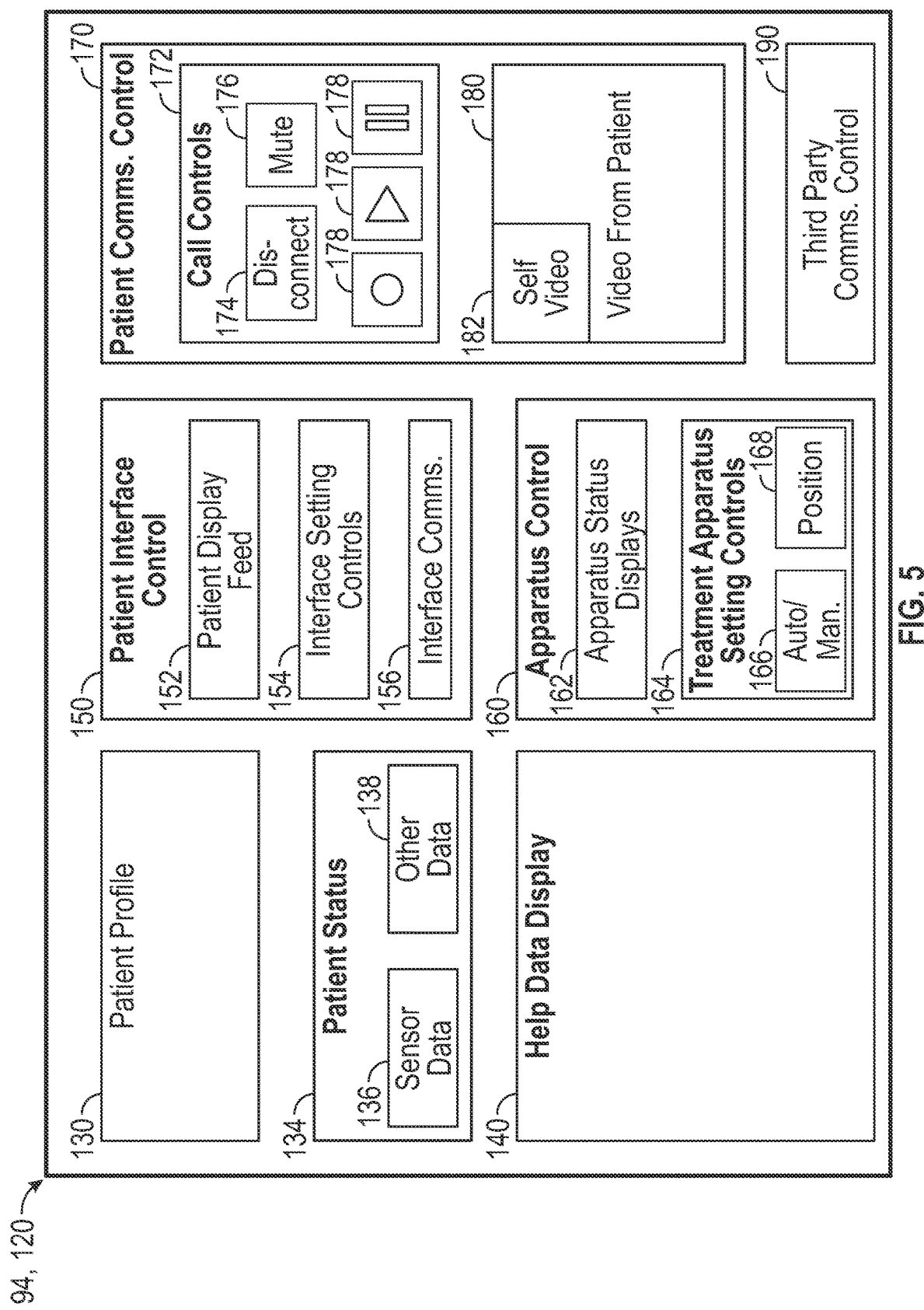
FIG. 5 generally illustrates an example embodiment of an overview display of an assistant interface according to the principles of the present disclosure.

FIG. 5 is an example embodiment of an overview display 120 of the assistant interface 94. Specifically, the overview display 120 presents several different controls and interfaces for the healthcare provider to remotely assist a patient with using the patient interface 50 and/or the treatment device 70. This remote assistance functionality may also be called telemedicine or telehealth.

Specifically, the overview display 120 includes a patient profile display 130 presenting biographical information regarding a patient using the treatment device 70. The patient profile display 130 may take the form of a portion or region of the overview display 120, as is generally illustrated in FIG. 5, although the patient profile display 130 may take other forms, such as a separate screen or a popup window.

In some embodiments, the patient profile display 130 may include a limited subset of the patient's biographical information. More specifically, the data presented upon the patient profile display 130 may depend upon the healthcare provider's need for that information. For example, a healthcare provider that is assisting the patient with a medical issue may be provided with medical history information regarding the patient, whereas a technician troubleshooting an issue with the treatment device 70 may be provided with a much more limited set of information regarding the patient. The technician, for example, may be given only the patient's name.

The patient profile display 130 may include pseudonymized data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject".

In some embodiments, the patient profile display 130 may present information regarding the treatment plan for the patient to follow in using the treatment device 70. Such treatment plan information may be limited to a healthcare provider. For example, a healthcare provider assisting the patient with an issue regarding the treatment regimen may be provided with treatment plan information, whereas a technician troubleshooting an issue with the treatment device 70 may not be provided with any information regarding the patient's treatment plan.

In some embodiments, one or more recommended treatment plans and/or excluded treatment plans may be presented in the patient profile display 130 to the healthcare provider. The one or more recommended treatment plans and/or excluded treatment plans may be generated by the artificial intelligence engine 11 of the server 30 and received from the server 30 in real-time during a telemedicine or telehealth session. An example of presenting the one or more recommended treatment plans and/or ruled-out treatment plans is described below with reference to FIG. 7.

The example overview display 120 generally illustrated in FIG. 5 also includes a patient status display 134 presenting status information regarding a patient using the treatment device. The patient status display 134 may take the form of a portion or region of the overview display 120, as is generally illustrated in FIG. 5, although the patient status display 134 may take other forms, such as a separate screen or a popup window.

The patient status display 134 includes sensor data 136 from one or more of the external sensors 82, 84, 86, and/or from one or more internal sensors 76 of the treatment device 70. In some embodiments, the patient status display 134 may include sensor data from one or more sensors of one or more wearable devices worn by the patient while using the treatment device 70. The one or more wearable devices may include a watch, a bracelet, a necklace, a chest strap, and the like. The one or more wearable devices may be configured to monitor a heartrate, a temperature, a blood pressure, one or more vital signs, and the like of the patient while the patient is using the treatment device 70. In some embodiments, the patient status display 134 may present other data 138 regarding the patient, such as last reported pain level, or progress within a treatment plan.

User access controls may be used to limit access, including what data is available to be viewed and/or modified, on any or all of the user interfaces 20, 50, 90, 92, 94 of the system 10. In some embodiments, user access controls may be employed to control what information is available to any given person using the system 10. For example, data presented on the assistant interface 94 may be controlled by user access controls, with permissions set depending on the healthcare provider/user's need for and/or qualifications to view that information.

The example overview display 120 generally illustrated in FIG. 5 also includes a help data display 140 presenting information for the healthcare provider to use in assisting the patient. The help data display 140 may take the form of a portion or region of the overview display 120, as is generally illustrated in FIG. 5. The help data display 140 may take other forms, such as a separate screen or a popup window. The help data display 140 may include, for example, presenting answers to frequently asked questions regarding use of the patient interface 50 and/or the treatment device 70.

The help data display 140 may also include research data or best practices. In some embodiments, the help data display 140 may present scripts for answers or explanations in response to patient questions. In some embodiments, the help data display 140 may present flow charts or walkthroughs for the healthcare provider to use in determining a root cause and/or solution to a patient's problem.

In some embodiments, the assistant interface 94 may present two or more help data displays 140, which may be the same or different, for simultaneous presentation of help data for use by the healthcare provider. for example, a first help data display may be used to present a troubleshooting flowchart to determine the source of a patient's problem, and a second help data display may present script information for the healthcare provider to read to the patient, such information to preferably include directions for the patient to perform some action, which may help to narrow down or solve the problem. In some embodiments, based upon inputs to the troubleshooting flowchart in the first help data display, the second help data display may automatically populate with script information.

The example overview display 120 generally illustrated in FIG. 5 also includes a patient interface control 150 presenting information regarding the patient interface 50, and/or to modify one or more settings of the patient interface 50. The patient interface control 150 may take the form of a portion or region of the overview display 120, as is generally illustrated in FIG. 5. The patient interface control 150 may take other forms, such as a separate screen or a popup window. The patient interface control 150 may present information communicated to the assistant interface 94 via one or more of the interface monitor signals 98*b*.

As is generally illustrated in FIG. 5, the patient interface control 150 includes a display feed 152 of the display presented by the patient interface 50. In some embodiments, the display feed 152 may include a live copy of the display screen currently being presented to the patient by the patient interface 50. In other words, the display feed 152 may present an image of what is presented on a display screen of the patient interface 50.

In some embodiments, the display feed 152 may include abbreviated information regarding the display screen currently being presented by the patient interface 50, such as a screen name or a screen number. The patient interface control 150 may include a patient interface setting control 154 for the healthcare provider to adjust or to control one or more settings or aspects of the patient interface 50. In some embodiments, the patient interface setting control 154 may cause the assistant interface 94 to generate and/or to transmit an interface control signal 98 for controlling a function or a setting of the patient interface 50.

In some embodiments, the patient interface setting control 154 may include collaborative browsing or co-browsing capability for the healthcare provider to remotely view and/or control the patient interface 50. For example, the patient interface setting control 154 may enable the healthcare provider to remotely enter text to one or more text entry fields on the patient interface 50 and/or to remotely control a cursor on the patient interface 50 using a mouse or touchscreen of the assistant interface 94.

In some embodiments, using the patient interface 50, the patient interface setting control 154 may allow the healthcare provider to change a setting that cannot be changed by the patient. For example, the patient interface 50 may be precluded from accessing a language setting to prevent a patient from inadvertently switching, on the patient interface 50, the language used for the displays, whereas the patient interface setting control 154 may enable the healthcare provider to change the language setting of the patient interface 50. In another example, the patient interface 50 may not be able to change a font size setting to a smaller size in order to prevent a patient from inadvertently switching the font size used for the displays on the patient interface 50 such that the display would become illegible to the patient, whereas the patient interface setting control 154 may provide for the healthcare provider to change the font size setting of the patient interface 50.

The example overview display 120 generally illustrated in FIG. 5 also includes an interface communications display 156 showing the status of communications between the patient interface 50 and one or more other devices 70, 82, 84, such as the treatment device 70, the ambulation sensor 82, and/or the goniometer 84. The interface communications display 156 may take the form of a portion or region of the overview display 120, as is generally illustrated in FIG. 5.

The interface communications display 156 may take other forms, such as a separate screen or a popup window. The interface communications display 156 may include controls for the healthcare provider to remotely modify communications with one or more of the other devices 70, 82, 84. For example, the healthcare provider may remotely command the patient interface 50 to reset communications with one of the other devices 70, 82, 84, or to establish communications with a new one of the other devices 70, 82, 84. This functionality may be used, for example, where the patient has a problem with one of the other devices 70, 82, 84, or where the patient receives a new or a replacement one of the other devices 70, 82, 84.

The example overview display 120 generally illustrated in FIG. 5 also includes an apparatus control 160 for the healthcare provider to view and/or to control information regarding the treatment device 70. The apparatus control 160 may take the form of a portion or region of the overview display 120, as is generally illustrated in FIG. 5. The apparatus control 160 may take other forms, such as a separate screen or a popup window. The apparatus control 160 may include an apparatus status display 162 with information regarding the current status of the apparatus. The apparatus status display 162 may present information communicated to the assistant interface 94 via one or more of the apparatus monitor signals 99*b*. The apparatus status display 162 may indicate whether the treatment device 70 is currently communicating with the patient interface 50. The apparatus status display 162 may present other current and/or historical information regarding the status of the treatment device 70.

The apparatus control 160 may include an apparatus setting control 164 for the healthcare provider to adjust or control one or more aspects of the treatment device 70. The apparatus setting control 164 may cause the assistant interface 94 to generate and/or to transmit an apparatus control signal 99 (e.g., which may be referred to as treatment plan input, as described) for changing an operating parameter and/or one or more characteristics of the treatment device 70, (e.g., a pedal radius setting, a resistance setting, a target RPM, other suitable characteristics of the treatment device 70, or a combination thereof).

The apparatus setting control 164 may include a mode button 166 and a position control 168, which may be used in conjunction for the healthcare provider to place an actuator 78 of the treatment device 70 in a manual mode, after which a setting, such as a position or a speed of the actuator 78, can be changed using the position control 168. The mode button 166 may provide for a setting, such as a position, to be toggled between automatic and manual modes.

In some embodiments, one or more settings may be adjustable at any time, and without having an associated auto/manual mode. In some embodiments, the healthcare provider may change an operating parameter of the treatment device 70, such as a pedal radius setting, while the patient is actively using the treatment device 70. Such "on the fly" adjustment may or may not be available to the patient using the patient interface 50.

In some embodiments, the mode button 166 may be configured to allow the healthcare provider and/or the patient to place the treatment device 70 in one of a plurality of modes. The modes may be referred to as treatment device modes. The plurality of treatment device modes may include a passive mode, an active-assisted mode, a resistive mode, an active mode, and/or other suitable mode. The passive mode may refer to an electric motor of the treatment device 70 independently driving the one or more radially-adjustable couplings rotationally coupled to the one or more pedals 102. In the passive mode, the electric motor may be the only source of driving force on the radially-adjustable couplings. That is, the patient may engage the pedals 102 with their hands or their feet and the electric motor may rotate the radially-adjustable couplings for the patient. This may enable moving the affected body part and stretching the affected body part for certain purposes, including, without limitation, increasing the patient's range of motion, without the patient exerting excessive force.

The active-assisted mode may refer to the electric motor receiving measurements of revolutions per minute of the one or more radially-adjustable couplings, and causing the electric motor 12 to drive the one or more radially-adjustable couplings rotationally coupled to the one or more pedals 102 when the measured revolutions per minute satisfy a threshold condition. The threshold condition may be configurable by the patient and/or the healthcare provider. The electric motor may be powered off while the user provides the driving force to the radially-adjustable couplings provided that the revolutions per minute are above a revolutions per minute threshold and the threshold condition is not satisfied. If the revolutions per minute are less than the revolutions per minute threshold, then the threshold condition is satisfied and the electric motor may be controlled to drive the radially-adjustable couplings to maintain the revolutions per minute threshold.

The resistive mode may refer to the electric motor providing resistance to rotation of the one or more radially-adjustable couplings coupled to the one or more pedals 102. The resistive mode may increase the strength, range of motion, pliability or other measurable property of the body part being rehabilitated by causing the muscle to exert force to move the pedals against the resistance provided by the electric motor.

The active mode may refer to the electric motor powering off such that it does not provide any driving force assistance to the radially-adjustable couplings. Instead, in this mode, using their hands or feet, for example, the user provides the sole driving force to the radially-adjustable couplings.

In some embodiments, the apparatus setting control 164 may allow the healthcare provider to change a setting that cannot be changed by the patient using the patient interface 50. For example, the patient interface 50 may be precluded from changing a preconfigured setting, such as a height or a tilt setting of the treatment device 70, whereas the apparatus setting control 164 may provide for the healthcare provider to change the height or tilt setting of the treatment device 70.

The example overview display 120 generally illustrated in FIG. 5 also includes a patient communications control 170 for controlling an audio or an audiovisual communications session with the patient interface 50. The communications session with the patient interface 50 may comprise a live feed from the assistant interface 94 for presentation by the output device of the patient interface 50. The live feed may take the form of an audio feed and/or a video feed. In some embodiments, the patient interface 50 may be configured to provide two-way audio or audiovisual communications with a person using the assistant interface 94. Specifically, the communications session with the patient interface 50 may include bidirectional (two-way) video or audiovisual feeds, with each of the patient interface 50 and the assistant interface 94 presenting video of the other one.

In some embodiments, the patient interface 50 may present video from the assistant interface 94, while the assistant interface 94 presents only audio or the assistant interface 94 presents no live audio or visual signal from the patient interface 50. In some embodiments, the assistant interface 94 may present video from the patient interface 50, while the patient interface 50 presents only audio or the patient interface 50 presents no live audio or visual signal from the assistant interface 94.

In some embodiments, the audio or an audiovisual communications session with the patient interface 50 may take place, at least in part, while the patient is performing the rehabilitation regimen upon the body part. The patient communications control 170 may take the form of a portion or region of the overview display 120, as is generally illustrated in FIG. 5. The patient communications control 170 may take other forms, such as a separate screen or a popup window.

The audio and/or audiovisual communications may be processed and/or directed by the assistant interface 94 and/or by another device or devices, such as a telephone system, or a videoconferencing system used by the healthcare provider while the healthcare provider uses the assistant interface 94. Alternatively or additionally, the audio and/or audiovisual communications may include communications with a third party. For example, the system 10 may enable the healthcare provider to initiate a 3-way conversation regarding use of a particular piece of hardware or software, with the patient and a subject matter expert, such as a healthcare provider or a specialist. The example patient communications control 170 generally illustrated in FIG. 5 includes call controls 172 for the healthcare provider to use in managing various aspects of the audio or audiovisual communications with the patient. The call controls 172 include a disconnect button 174 for the healthcare provider to end the audio or audiovisual communications session. The call controls 172 also include a mute button 176 to temporarily silence an audio or audiovisual signal from the assistant interface 94. In some embodiments, the call controls 172 may include other features, such as a hold button (not shown).

The call controls 172 also include one or more record/playback controls 178, such as record, play, and pause buttons to control, with the patient interface 50, recording and/or playback of audio and/or video from the teleconference session. The call controls 172 also include a video feed display 180 for presenting still and/or video images from the patient interface 50, and a self-video display 182 showing the current image of the healthcare provider using the assistant interface 94. The self-video display 182 may be presented as a picture-in-picture format, within a section of the video feed display 180, as is generally illustrated in FIG. 5. Alternatively or additionally, the self-video display 182 may be presented separately and/or independently from the video feed display 180.

The example overview display 120 generally illustrated in FIG. 5 also includes a third party communications control 190 for use in conducting audio and/or audiovisual communications with a third party. The third party communications control 190 may take the form of a portion or region of the overview display 120, as is generally illustrated in FIG. 5. The third party communications control 190 may take other forms, such as a display on a separate screen or a popup window.

The third party communications control 190 may include one or more controls, such as a contact list and/or buttons or controls to contact a third party regarding use of a particular piece of hardware or software, e.g., a subject matter expert, such as a healthcare provider or a specialist. The third party communications control 190 may include conference calling capability for the third party to simultaneously communicate with both the healthcare provider via the assistant interface 94, and with the patient via the patient interface 50. For example, the system 10 may provide for the healthcare provider to initiate a 3-way conversation with the patient and the third party.

Figure 6:
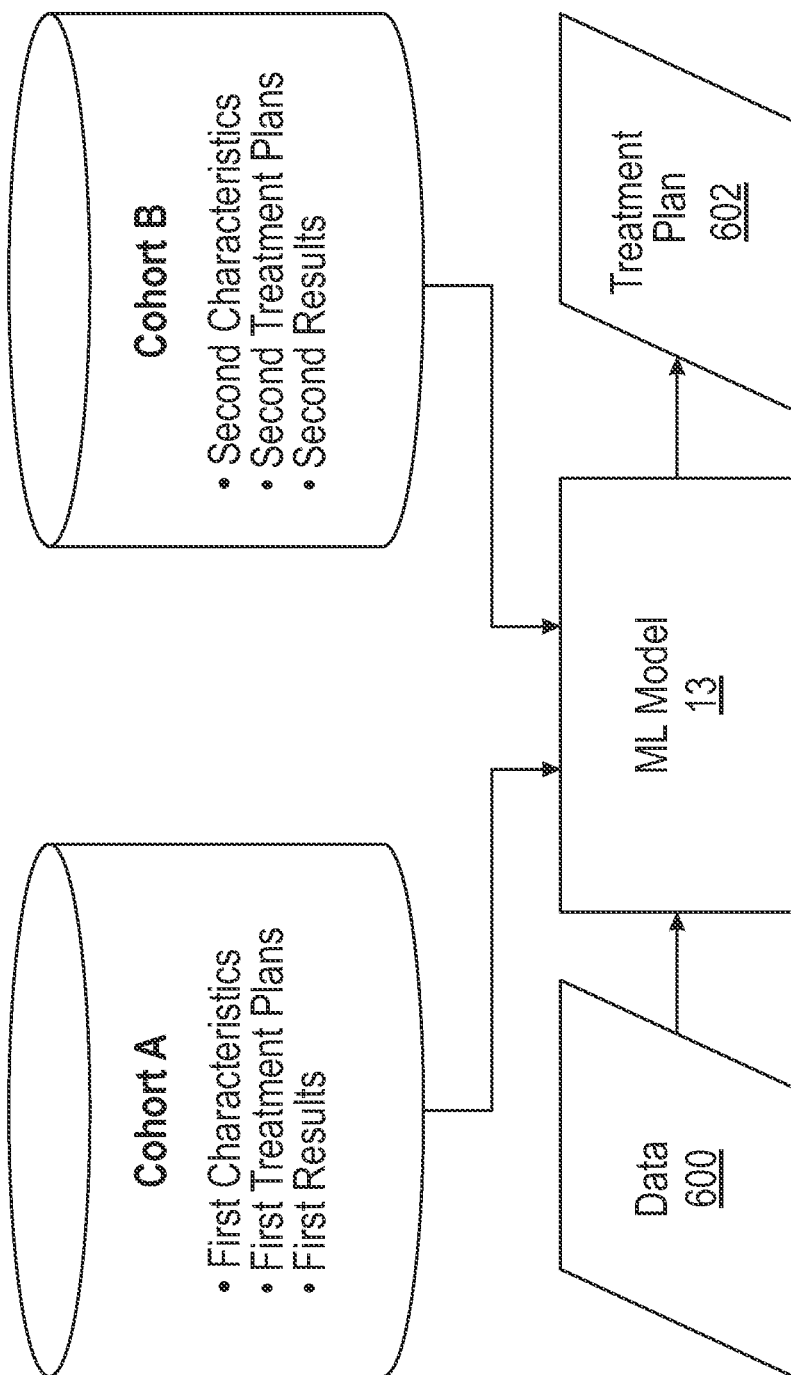
FIG. 6 generally illustrates an example block diagram of training a machine learning model to output, based on data pertaining to the patient, a treatment plan for the patient according to the principles of the present disclosure.

FIG. 6 generally illustrates an example block diagram of training a machine learning model 13 to output, based on data 600 pertaining to the patient, a treatment plan 602 for the patient according to the present disclosure. Data pertaining to other patients may be received by the server 30. The other patients may have used various treatment devices to perform treatment plans.

The data may include characteristics of the other patients, the details of the treatment plans performed by the other patients, and/or the results of performing the treatment plans (e.g., a percent of recovery of a portion of the patients' bodies, an amount of recovery of a portion of the patients' bodies, an amount of increase or decrease in muscle strength of a portion of patients' bodies, an amount of increase or decrease in range of motion of a portion of patients' bodies, etc.).

As depicted, the data has been assigned to different cohorts. Cohort A includes data for patients having similar first characteristics, first treatment plans, and first results. Cohort B includes data for patients having similar second characteristics, second treatment plans, and second results. For example, cohort A may include first characteristics of patients in their twenties without any medical conditions who underwent surgery for a broken limb; their treatment plans may include a certain treatment protocol (e.g., use the treatment device 70 for 30 minutes 5 times a week for 3 weeks, wherein values for the properties, configurations, and/or settings of the treatment device 70 are set to X (where X is a numerical value) for the first two weeks and to Y (where Y is a numerical value) for the last week).

Cohort A and cohort B may be included in a training dataset used to train the machine learning model 13. The machine learning model 13 may be trained to match a pattern between characteristics for each cohort and output the treatment plan or a variety of possible treatment plans for selection by a healthcare provider that provides the result. Accordingly, when the data 600 for a new patient is input into the trained machine learning model 13, the trained machine learning model 13 may match the characteristics included in the data 600 with characteristics in either cohort A or cohort B and output the appropriate treatment plan or plans 602. In some embodiments, the machine learning model 13 may be trained to output one or more excluded treatment plans that should not be performed by the new patient.

Figure 7:
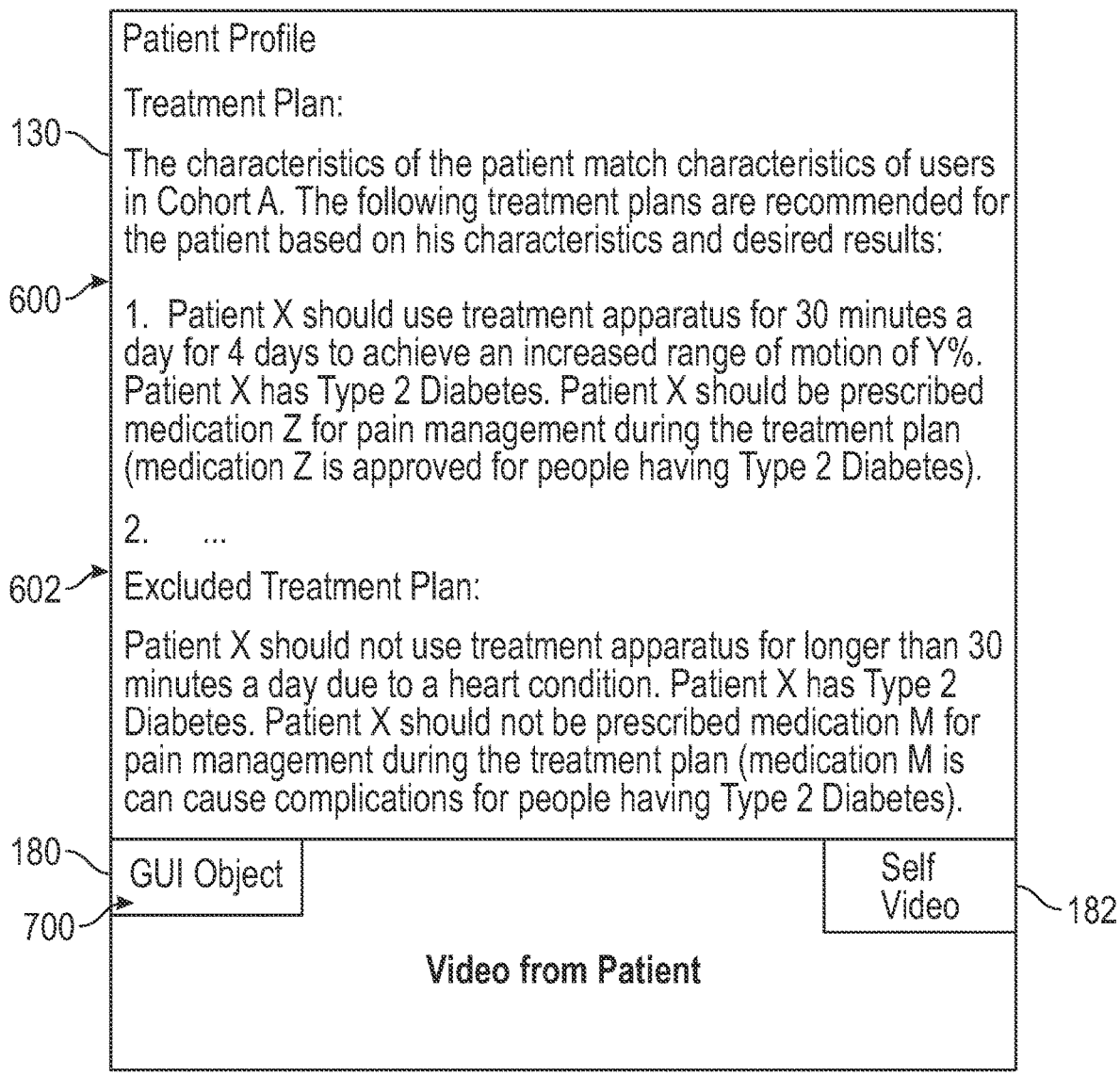
FIG. 7 generally illustrates an embodiment of an overview display of the assistant interface presenting recommended treatment plans and excluded treatment plans in real-time during a telemedicine session according to the principles of the present disclosure.

FIG. 7 generally illustrates an embodiment of an overview display 120 of the assistant interface 94 presenting recommended treatment plans and excluded treatment plans in real-time during a telemedicine session according to the present disclosure. As depicted, the overview display 120 just includes sections for the patient profile 130 and the video feed display 180, including the self-video display 182. Any suitable configuration of controls and interfaces of the overview display 120 described with reference to FIG. 5 may be presented in addition to or instead of the patient profile 130, the video feed display 180, and the self-video display 182.

The healthcare provider using the assistant interface 94 (e.g., computing device) during the telemedicine session may be presented in the self-video 182 in a portion of the overview display 120 (e.g., user interface presented on a display screen 24 of the assistant interface 94) that also presents a video from the patient in the video feed display 180. Further, the video feed display 180 may also include a graphical user interface (GUI) object 700 (e.g., a button) that enables the healthcare provider to share, in real-time or near real-time during the telemedicine session, the recommended treatment plans and/or the excluded treatment plans with the patient on the patient interface 50. The healthcare provider may select the GUI object 700 to share the recommended treatment plans and/or the excluded treatment plans. As depicted, another portion of the overview display 120 includes the patient profile display 130.

The patient profile display 130 is presenting two example recommended treatment plans 600 and one example excluded treatment plan 602. As described herein, the treatment plans may be recommended in view of characteristics of the patient being treated. To generate the recommended treatment plans 600 the patient should follow to achieve a desired result, a pattern between the characteristics of the patient being treated and a cohort of other people who have used the treatment device 70 to perform a treatment plan may be matched by one or more machine learning models 13 of the artificial intelligence engine 11. Each of the recommended treatment plans may be generated based on different desired results.

For example, as depicted, the patient profile display 130 presents "The characteristics of the patient match characteristics of uses in Cohort A. The following treatment plans are recommended for the patient based on his characteristics and desired results." Then, the patient profile display 130 presents recommended treatment plans from cohort A, and each treatment plan provides different results.

As depicted, treatment plan "A" indicates "Patient X should use treatment device for 30 minutes a day for 4 days to achieve an increased range of motion of Y %; Patient X has Type 2 Diabetes; and Patient X should be prescribed medication Z for pain management during the treatment plan (medication Z is approved for people having Type 2 Diabetes)." Accordingly, the treatment plan generated achieves increasing the range of motion of Y %. As may be appreciated, the treatment plan also includes a recommended medication (e.g., medication Z) to prescribe to the patient to manage pain in view of a known medical disease (e.g., Type 2 Diabetes) of the patient. That is, the recommended patient medication not only does not conflict with the medical condition of the patient but thereby improves the probability of a superior patient outcome. This specific example and all such examples elsewhere herein are not intended to limit in any way the generated treatment plan from recommending multiple medications, or from handling the acknowledgement, view, diagnosis and/or treatment of comorbid conditions or diseases.

Recommended treatment plan "B" may specify, based on a different desired result of the treatment plan, a different treatment plan including a different treatment protocol for a treatment device, a different medication regimen, etc.

As depicted, the patient profile display 130 may also present the excluded treatment plans 602. These types of treatment plans are shown to the healthcare provider using the assistant interface 94 to alert the healthcare provider not to recommend certain portions of a treatment plan to the patient. For example, the excluded treatment plan could specify the following: "Patient X should not use treatment device for longer than 30 minutes a day due to a heart condition; Patient X has Type 2 Diabetes; and Patient X should not be prescribed medication M for pain management during the treatment plan (in this scenario, medication M can cause complications for people having Type 2 Diabetes). Specifically, the excluded treatment plan points out a limitation of a treatment protocol where, due to a heart condition, Patient X should not exercise for more than 30 minutes a day. The ruled-out treatment plan also points out that Patient X should not be prescribed medication M because it conflicts with the medical condition Type 2 Diabetes.

The healthcare provider may select the treatment plan for the patient on the overview display 120. For example, the healthcare provider may use an input peripheral (e.g., mouse, touchscreen, microphone, keyboard, etc.) to select from the treatment plans 600 for the patient. In some embodiments, during the telemedicine session, the healthcare provider may discuss the pros and cons of the recommended treatment plans 600 with the patient.

In any event, the healthcare provider may select the treatment plan for the patient to follow to achieve the desired result. The selected treatment plan may be transmitted to the patient interface 50 for presentation. The patient may view the selected treatment plan on the patient interface 50. In some embodiments, the healthcare provider and the patient may discuss during the telemedicine session the details (e.g., treatment protocol using treatment device 70, diet regimen, medication regimen, etc.) in real-time or in near real-time. In some embodiments, the server 30 may control, based on the selected treatment plan and during the telemedicine session, the treatment device 70 as the user uses the treatment device 70.

Figure 8:
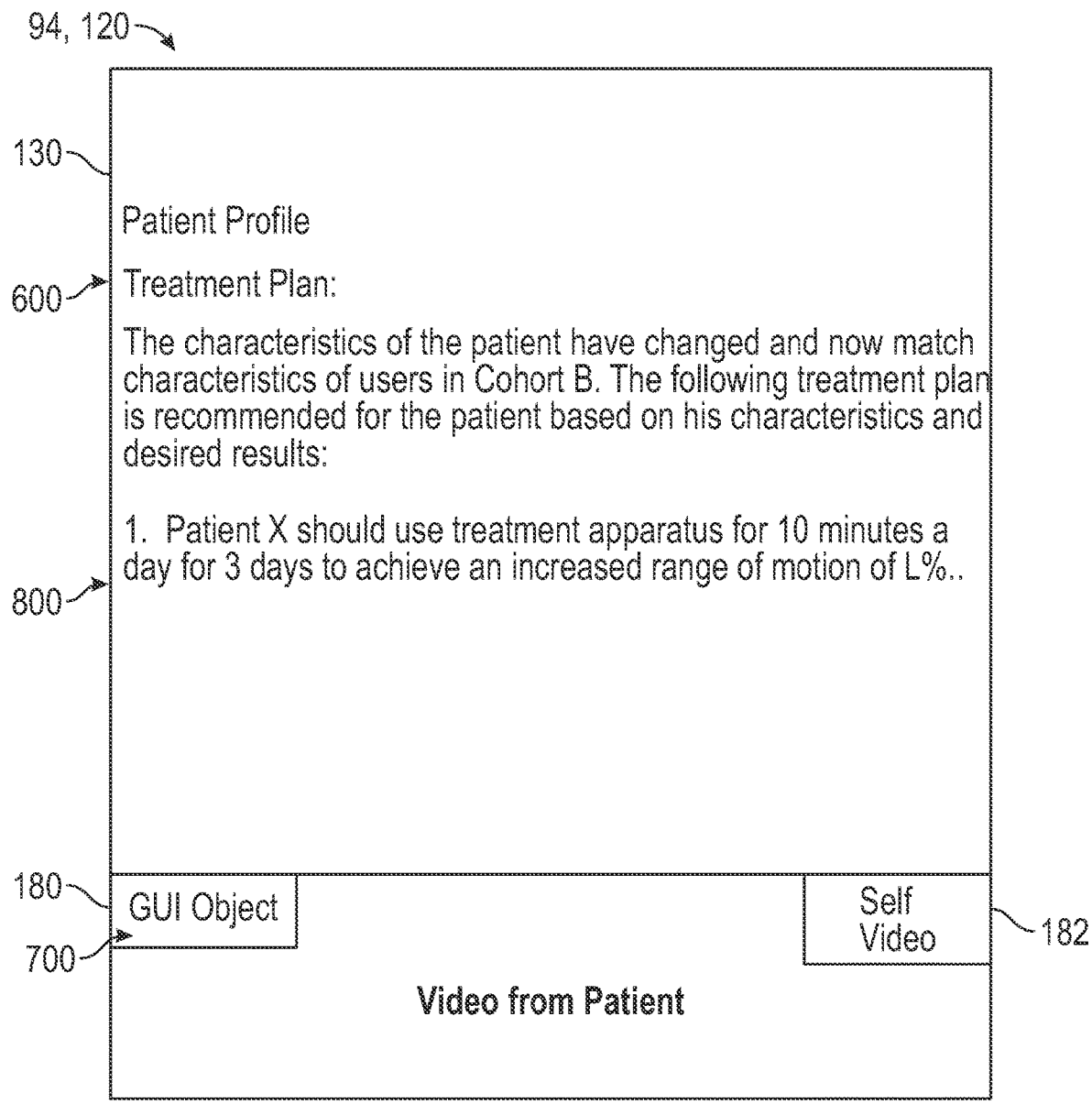
FIG. 8 generally illustrates an embodiment of the overview display of the assistant interface presenting, in real-time during a telemedicine session, recommended treatment plans that have changed as a result of patient data changing according to the principles of the present disclosure.

FIG. 8 generally illustrates an embodiment of the overview display 120 of the assistant interface 94 presenting, in real-time during a telemedicine session, recommended treatment plans that have changed as a result of patient data changing according to the present disclosure. As may be appreciated, the treatment device 70 and/or any computing device (e.g., patient interface 50) may transmit data while the patient uses the treatment device 70 to perform a treatment plan. The data may include updated characteristics of the patient and/or other treatment data. For example, the updated characteristics may include new performance information and/or measurement information. The performance information may include a speed of a portion of the treatment device 70, a range of motion achieved by the patient, a force exerted on a portion of the treatment device 70, a heartrate of the patient, a blood pressure of the patient, a respiratory rate of the patient, and so forth.

In some embodiments, the data received at the server 30 may be input into the trained machine learning model 13, which may determine that the characteristics indicate the patient is on track for the current treatment plan. Determining the patient is on track for the current treatment plan may cause the trained machine learning model 13 to adjust a parameter of the treatment device 70. The adjustment may be based on a next step of the treatment plan to further improve the performance of the patient.

In some embodiments, the data received at the server 30 may be input into the trained machine learning model 13, which may determine that the characteristics indicate the patient is not on track (e.g., behind schedule, not able to maintain a speed, not able to achieve a certain range of motion, is in too much pain, etc.) for the current treatment plan or is ahead of schedule (e.g., exceeding a certain speed, exercising longer than specified with no pain, exerting more than a specified force, etc.) for the current treatment plan.

The trained machine learning model 13 may determine that the characteristics of the patient no longer match the characteristics of the patients in the cohort to which the patient is assigned. Accordingly, the trained machine learning model 13 may reassign the patient to another cohort that includes qualifying characteristics the patient's characteristics. As such, the trained machine learning model 13 may select a new treatment plan from the new cohort and control, based on the new treatment plan, the treatment device 70.

In some embodiments, prior to controlling the treatment device 70, the server 30 may provide the new treatment plan 800 to the assistant interface 94 for presentation in the patient profile 130. As depicted, the patient profile 130 indicates "The characteristics of the patient have changed and now match characteristics of uses in Cohort B. The following treatment plan is recommended for the patient based on his characteristics and desired results." Then, the patient profile 130 presents the new treatment plan 800 ("Patient X should use the treatment device for 10 minutes a day for 3 days to achieve an increased range of motion of L %." The healthcare provider may select the new treatment plan 800, and the server 30 may receive the selection. The server 30 may control the treatment device 70 based on the new treatment plan 800. In some embodiments, the new treatment plan 800 may be transmitted to the patient interface 50 such that the patient may view the details of the new treatment plan 800.

In some embodiments, the server 30 may be configured to receive treatment data pertaining to a user using the treatment device 70 to perform a treatment plan. The user may include a patient, user, or person using the treatment device 70 to perform various exercises. The treatment data may include various characteristics of the user, various measurement information pertaining to the user while the user uses the treatment device 70, various characteristics of the treatment device 70, the treatment plan, other suitable data, or a combination thereof. The server 30 may receive the treatment data during a telemedicine session.

In some embodiments, while the user uses the treatment device 70 to perform the treatment plan, at least some of the treatment data may include the sensor data 136 from one or more of the external sensors 82, 84, 86, and/or from one or more internal sensors 76 of the treatment device 70. Any sensor referred to herein may be standalone, part of a neural net, a node on the Internet of Things, or otherwise connected or configured to be connected to a physical or wireless network.

In some embodiments, at least some of the treatment data may include sensor data from one or more sensors of one or more wearable devices worn by the user while using the treatment device 70. The one or more wearable devices may include a watch, a bracelet, a necklace, a headband, a wristband, an ankle band, eyeglasses or eyewear (such as, without limitation, Google Glass) a chest or torso strap, a device configured to be worked on, attached to, or communicatively coupled to a body, and the like. While the user is using the treatment device 70, the one or more wearable devices may be configured to monitor, with respect to the user, a heartrate, a temperature, a blood pressure, an eye dilation, one or more vital signs, one or more metabolic markers, biomarkers, and the like.

In some embodiments, at least some of the treatment data may include sensor data from one or more sensors of one or more sensing or Internet of Things (IoT) devices. Such devices may be near the user but not worn by the user. Additionally, or alternatively, such devices may be configured to sense, measure, obtain, or otherwise monitor, with respect to the user, a heartrate, a temperature, a blood pressure, an eye dilation, one or more vital signs, one or more metabolic markers, biomarkers, and the like. In some embodiments, such devices may be configured to generate a sensing field that wholly or partially encapsulates the user or that is otherwise communicatively coupled to the user. The devices may be configured to sense, measure, obtain, or otherwise monitor, with respect to the user while the user is in the sensing field, a heartrate, a temperature, a blood pressure, an eye dilation, one or more vital signs, one or more metabolic markers, biomarkers, and the like.

The various characteristics of the treatment device 70 may include one or more settings of the treatment device 70, a current revolutions per time period (e.g., such as one minute)

of a rotating member (e.g., such as a wheel) of the treatment device 70, a resistance setting of the treatment device 70, other suitable characteristics of the treatment device 70, or a combination thereof. The measurement information may include one or more vital signs of the user, a respiration rate of the user, a heartrate of the user, a temperature of the user, an SpO2-measurement of the blood oxygen level of the user (e.g., oxygen saturation level), a blood pressure of the user, a glucose level of the user, other suitable measurement information of the user, microbiome related data pertaining to the user, or a combination thereof.

In some embodiments, the server 30 may identify, using at least one aspect of the treatment data, at least one aspect associated with a first treatment device mode of the treatment device 70 of the at least one measurement pertaining to the user. The first treatment device mode may include any suitable mode of the treatment device 70, including those described herein.

In some embodiments, the server 30 may determine whether the at least one aspect of the at least one measurement pertaining to the user associated with the first treatment device mode of the treatment device 70 correlates with at least one secondary condition of the user. The at least one secondary condition may include any condition for which the user is not being treated while using the treatment device 70 (e.g., conditions not currently being treated and/or conditions of which the healthcare provider and/or the patient is unaware). It should be understood that the systems and methods described herein may use at least one other aspect and/or the at least one aspect of the at least one measurement and/or at least one other measurement pertaining to the user, wherein the aspect or aspects are associated with at least one other treatment device mode of the treatment device 70 in addition to or instead of the first treatment device mode, to determine secondary conditions of the user.

In some embodiments, by writing to an associated memory (e.g., such as the memory 62 or other suitable memory), the server 30 may determine whether the at least one aspect of the at least one measurement pertaining to the user associated with the first treatment device mode of the treatment device 70 is correlated with the at least one secondary condition, the at least one aspect of the at least one measurement pertaining to the user associated with the first treatment device mode of the treatment device 70.

The associated memory may be configured to be accessed by an artificial intelligence engine, such as the artificial intelligence engine 11. The artificial intelligence engine 11 may be configured to use at least one machine learning model, such as the machine learning model 13 or other suitable machine learning model, to generate, using the at least one aspect of the at least one measurement pertaining to the user associated with the first treatment device mode of the treatment device 70, at least one of secondary condition output prediction.

In some embodiments, the artificial intelligence engine 11 may use the machine learning model 13 to generate, further using secondary condition information associated with other users, the at least one of secondary condition output prediction. At least some of the other users may be associated with a cohort to which the user belongs; alternatively, all of the other users may be associated with the cohort of which the user belongs; further alternatively, the other users may be associated with other cohorts; or the other users may not be associated with cohorts. In some embodiments, the other users may have characteristics similar to those of the user. In some embodiments, measurements pertaining to the other users may include measurements similar to the at least one measurement pertaining to the user.

The at least one secondary condition output prediction generated by the machine learning model 13 may indicate one or more secondary conditions that may be associated with the user. For example, the machine learning model 13 may determine, based on the at least one aspect of the at least one measurement pertaining to the user associated with the first treatment device mode of the treatment device 70, that a predicted secondary condition may be affecting the user. The at least one secondary condition output prediction may include a probabilistic prediction (using, for example and without limitation, parametric, non-parametric, Bayesian and/or Markovian probabilistic methods), a stochastic prediction ((using, for example and without limitation, non-deterministic finite state automata), or a deterministic prediction (using, for example and without limitation, finite state automata). The server 30 may receive, from the artificial intelligence engine, the at least one secondary condition output prediction.

In some embodiments, in response to a determination that the at least one aspect of the at least one measurement pertaining to the user associated with the first treatment device mode of the treatment device 70 is correlated with the at least one secondary condition of the user, the server 30 may generate secondary condition information indicating at least the secondary condition. The server 30 may write the secondary condition information to an associated memory, such as the memory 62 or other suitable memory, for access at a computing device of a healthcare provider. For example, the server 30 may provide the secondary condition information to an interface, such as the interface 94 or other suitable interface, configured to present the secondary condition information to the healthcare provider. The interface may include a graphical user interface configured to provide the secondary condition information and to receive input from the healthcare provider. The healthcare provider may review or analyze the secondary condition information and determine whether to pursue treatment of the secondary condition indicated by the secondary condition information. Pursuing treatment of the secondary condition may include revising at least one aspect of the treatment plan or other suitable action.

In some embodiments, the treatment plan, including the configurations, settings, range of motion settings, pain level, force settings, and speed settings, etc. of the treatment device 70 for various exercises, may be transmitted to the controller of the treatment device 70. In one example, if the user provides an indication, via the patient interface 50, that he is experiencing a high level of pain at a particular range of motion, the controller may receive the indication. Based on the indication, the controller may electronically adjust the range of motion of the pedal 102 by adjusting the pedal inwardly, outwardly, or along or about any suitable axis, via one or more actuators, hydraulics, springs, electric motors, or the like. The treatment plan may define alternative range of motion settings for the pedal 102 when the user indicates certain pain levels during an exercise. Accordingly, once the treatment plan is uploaded to the controller of the treatment device 70, the treatment device 70 may continue to operate without further instruction, further external input, and the like. It should be noted that the patient (via the patient interface 50) and/or the assistant (via the assistant interface 94) may override any of the configurations or settings of the treatment device 70 at any time. For example, the patient may use the patient interface 50 to cause the treatment device 70 to immediately stop, if so desired.

Figure 9:
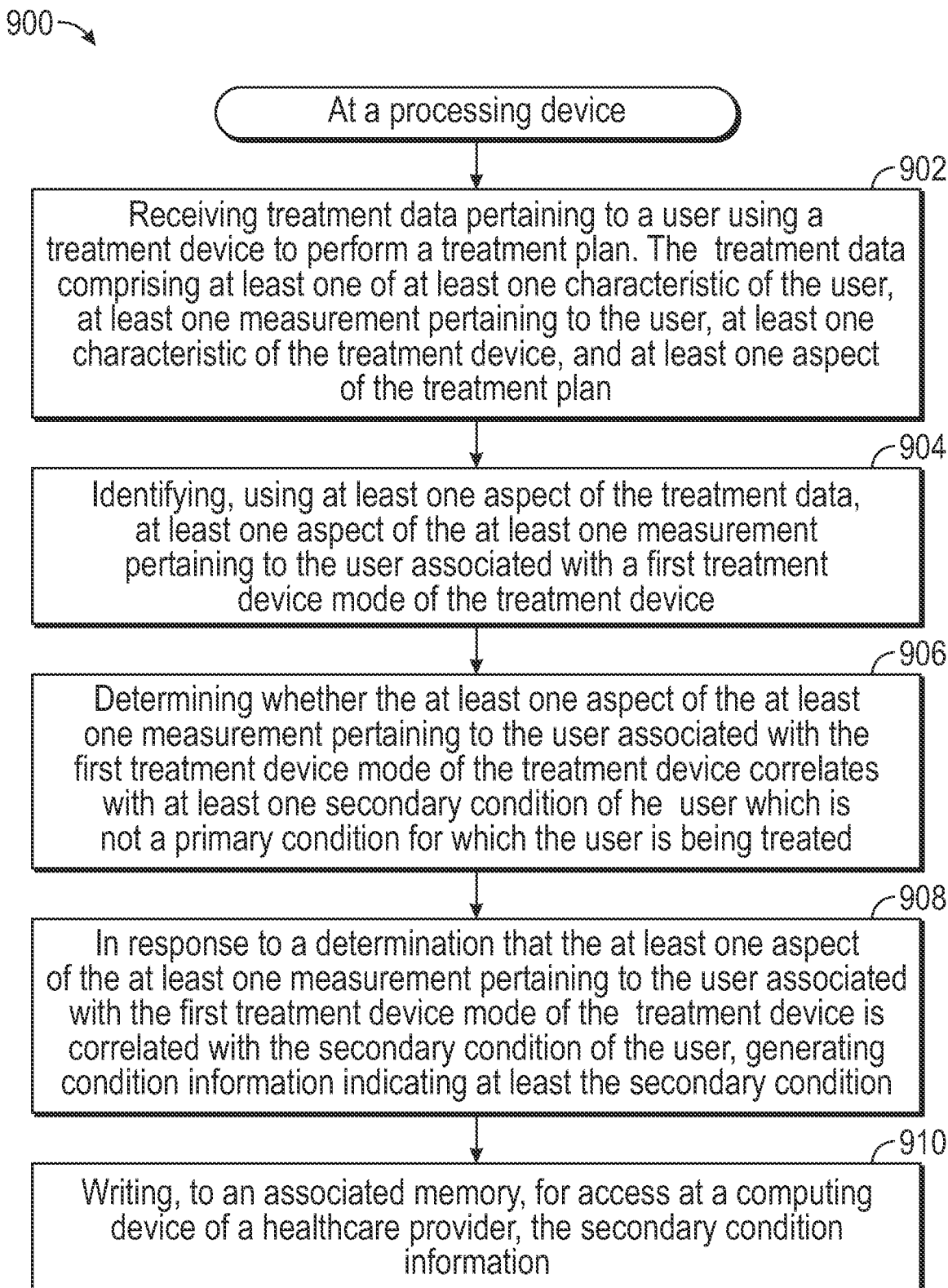
FIG. 9 is a flow diagram generally illustrating a method for identifying, based on treatment data pertaining to a user who uses the treatment device of FIG. 2, a secondary condition, which differs from a primary condition for which the user is being treated according to the principles of the present disclosure.

FIG. 9 is a flow diagram generally illustrating a method 900 identifying, based on treatment data pertaining to a user who uses the treatment device 70, a secondary condition, which differs from a primary condition for which the user is being treated (e.g., conditions not currently being treated and/or conditions of which the healthcare provider and/or the patient is unaware), according to the principles of the present disclosure. The method 900 is performed by processing logic that may include hardware (circuitry, dedicated logic, etc.), software (such as is run on a general-purpose computer system or a dedicated machine), or a combination of both. The method 900 and/or each of its individual functions, routines, subroutines, or operations may be performed by one or more processors of a computing device (e.g., any component of FIG. 1, such as server 30 executing the artificial intelligence engine 11). In some embodiments, the method 900 may be performed by a single processing thread. Alternatively, the method 900 may be performed by two or more processing threads, each thread implementing one or more individual functions, routines, subroutines, or operations of the methods.

For simplicity of explanation, the method 900 is depicted and described as a series of operations. However, operations in accordance with this disclosure can occur in various orders and/or concurrently, and/or with other operations not presented and described herein. For example, the operations depicted in the method 900 may occur in combination with any other operation of any other method disclosed herein. Furthermore, not all illustrated operations may be required to implement the method 900 in accordance with the disclosed subject matter. In addition, those skilled in the art will understand and appreciate that the method 900 could alternatively be represented as a series of interrelated states via a state diagram or events.

At 902, the processing device may receive treatment data pertaining to a user using a treatment device, such as the treatment device 70, to perform a treatment plan. The treatment data may include at least one of at least one characteristic of the user, at least one measurement pertaining to the user, at least one characteristic of the treatment device, and at least one aspect of the treatment plan.

At 904, the processing deice may identify, using at least one aspect of the treatment data associated with a first treatment device mode of the treatment device 70, at least one aspect of the at least one measurement pertaining to the user.

At 906, the processing device may determine whether the at least one aspect of the at least one measurement pertaining to the user associated with the first treatment device mode of the treatment device 70 correlates with at least one secondary condition of the user, wherein the at least one secondary condition of the user is not a primary condition for which the user is being treated (e.g., conditions not currently being treated and/or conditions of which the healthcare provider and/or the patient is unaware).

At 908, the processing device may, in response to a determination that the at least one aspect of the at least one measurement pertaining to the user associated with the first treatment device mode of the treatment device 70 is correlated with the at least one secondary condition of the user, generate secondary condition information indicating at least the secondary condition.

At 910, the processing device may write the secondary condition information to an associated memory, such as the memory 62 or other suitable memory, for access at a computing device of a healthcare provider.

Figure 10:
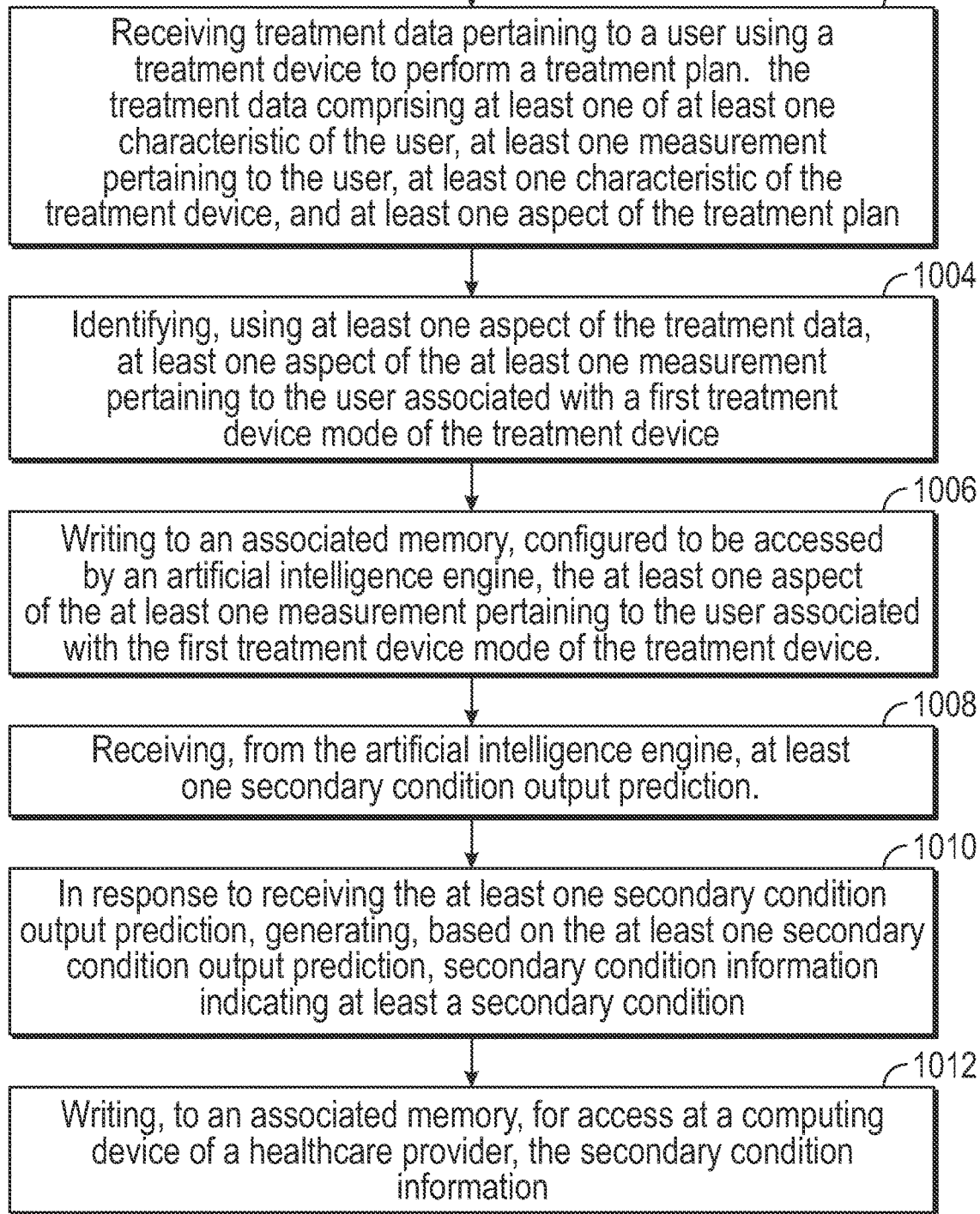
FIG. 10 is a flow diagram generally illustrating an alternative method for identifying, based on treatment data pertaining to a user who uses the treatment device of FIG. 2, a secondary condition, which differs from a primary condition for which the user is being treated according to the principles of the present disclosure.

FIG. 10 is a flow diagram generally illustrating an alternative method 1000 for identifying, based on treatment data pertaining to a user who uses the treatment device 70, a secondary condition, which differs from a primary condition for which the user is being treated (e.g., conditions not currently being treated and/or conditions of which the healthcare provider and/or the patient is unaware), according to the principles of the present disclosure. Method 1000 includes operations performed by processors of a computing device (e.g., any component of FIG. 1, such as server 30 executing the artificial intelligence engine 11). In some embodiments, one or more operations of the method 1000 are implemented in computer instructions stored on a memory device and executed by a processing device. The method 1000 may be performed in the same or a similar manner as described above in regard to method 900. The operations of the method 1000 may be performed in some combination with any of the operations of any of the methods described herein.

At 1002, the processing device may receive treatment data pertaining to a user using a treatment device, such as the treatment device 70, to perform a treatment plan. The treatment data may include at least one of at least one characteristic of the user, at least one measurement pertaining to the user, at least one characteristic of the treatment device, and at least one aspect of the treatment plan.

At 1004, the processing device may identify, using at least one aspect of the treatment data associated with a first treatment device mode of the treatment device 70, at least one aspect of the at least one measurement pertaining to the user.

At 1006, the processing device may write to an associated memory, such as the memory 62 or other suitable memory, the at least one aspect of the at least one measurement pertaining to the user associated with the first treatment device mode of the treatment device 70. The associated memory may be configured to be accessed by an artificial intelligence engine, such as the artificial intelligence engine 11. The artificial intelligence engine 11 may be configured to use at least one machine learning model, such as the machine learning model 13, to generate a secondary condition output prediction indicating at least one secondary condition.

At 1008, the processing device may receive, from the artificial intelligence engine 11, the at least one secondary condition output prediction.

At 1010, the processing device may, in response to receiving the at least one secondary condition output prediction, generate, based on the at least one secondary condition output prediction, secondary condition information indicating at least one secondary condition. The at least one secondary condition may include a condition affecting the user which is not the primary condition for while the user is being treated (e.g., conditions not currently being treated and/or conditions of which the healthcare provider and/or the patient is unaware).

At 1012, the processing device may write the secondary condition information to an associated memory, such as the memory 62 or other suitable memory, for access at a computing device of a healthcare provider.

Figure 11:
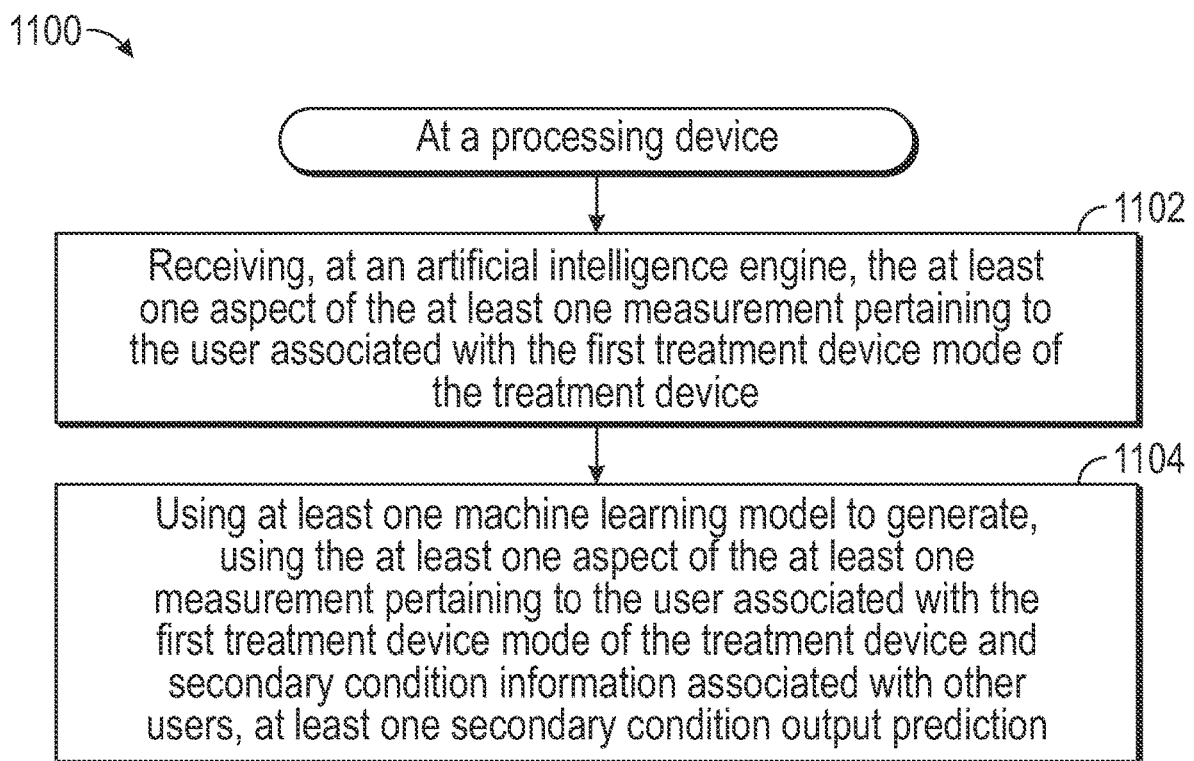
FIG. 11 is a flow diagram generally illustrating an alternative method for identifying, based on treatment data pertaining to a user who uses the treatment device of FIG. 2, a secondary condition, which differs from a primary condition for which the user is being treated according to the principles of the present disclosure.

FIG. 11 is a flow diagram generally illustrating an alternative method 1100 for identifying, based on treatment data pertaining to a user who uses the treatment device 70, a secondary condition, wherein such condition differs from a primary condition for which the user is being treated (e.g., conditions not currently being treated and/or conditions of which the healthcare provider and/or the patient is unaware), according to the principles of the present disclosure. Method 1100 includes operations performed by processors of a computing device (e.g., any component of FIG. 1, such as server 30 executing the artificial intelligence engine 11). In some embodiments, one or more operations of the method 1100 are implemented in computer instructions stored on a memory device and executed by a processing device. The method 1100 may be performed in the same or a similar manner as described above in regard to method 900 and/or method 1000. The operations of the method 1100 may be performed in some combination with any of the operations of any of the methods described herein.

At 1102, the artificial intelligence engine 11 may receive the at least one aspect of the at least one measurement pertaining to the user associated with the first treatment device mode of the treatment device 70.

Figure 12:
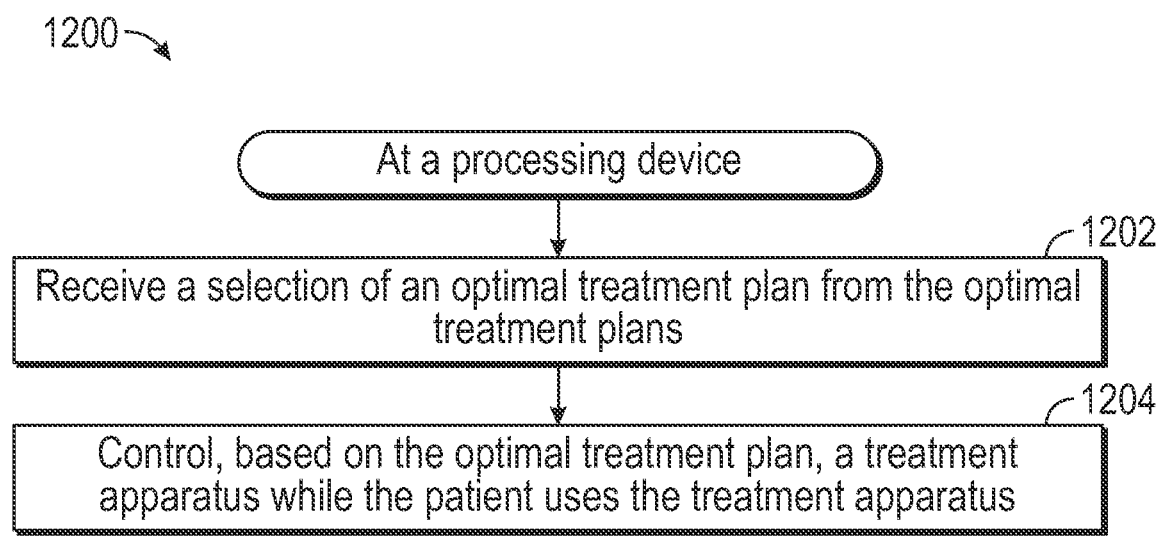
FIG. 12 is a flow diagram generally illustrating a method for receiving a selection of an optimal treatment plan and controlling, based on the optimal treatment plan, a treatment device while the patient uses the treatment device according to the present disclosure.

At 1104, the artificial intelligence engine 11 may use at least one machine learning model, such as the machine learning model 13 or other suitable machine learning model, to generate, using the at least one aspect of the at least one measurement pertaining to the user associated with the first treatment device mode of the treatment device 70 and secondary condition information associated with other users, at least one secondary condition output prediction. FIG. 12 generally illustrates an example embodiment of a method 1200 for receiving a selection of an optimal treatment plan and controlling a treatment device while the patient uses the treatment device according to the present disclosure, based on the optimal treatment plan. Method 1200 includes operations performed by processors of a computing device (e.g., any component of FIG. 1, such as server 30 executing the artificial intelligence engine 11). In some embodiments, one or more operations of the method 1200 are implemented in computer instructions stored on a memory device and executed by a processing device. The method 1200 may be performed in the same or a similar manner as described above in regard to method 900. The operations of the method 1200 may be performed in some combination with any of the operations of any of the methods described herein.

Prior to the method 1200 being executed, various optimal treatment plans may be generated by one or more trained machine learning models 13 of the artificial intelligence engine 11. For example, based on a set of treatment plans pertaining to a medical condition of a patient, the one or more trained machine learning models 13 may generate the optimal treatment plans. The various treatment plans may be transmitted to one or more computing devices of a patient and/or medical professional.

At 1202 of the method 1200, the processing device may receive a selection of an optimal treatment plan from the optimal treatment plans. The selection may have been entered on a user interface presenting the optimal treatment plans on the patient interface 50 and/or the assistant interface 94.

At 1204, the processing device may control, while the patient uses the treatment device 70, based on the selected optimal treatment plan, the treatment device 70. In some embodiments, the controlling is performed distally by the server 30. For example, if the selection is made using the patient interface 50, one or more control signals may be transmitted from the patient interface 50 to the treatment device 70 to configure, according to the selected treatment plan, a setting of the treatment device 70 to control operation of the treatment device 70. Further, if the selection is made using the assistant interface 94, one or more control signals may be transmitted from the assistant interface 94 to the treatment device 70 to configure, according to the selected treatment plan, a setting of the treatment device 70 to control operation of the treatment device 70.

It should be noted that, as the patient uses the treatment device 70, the sensors 76 may transmit measurement data to a processing device. The processing device may dynamically control, according to the treatment plan, the treatment device 70 by modifying, based on the sensor measurements, a setting of the treatment device 70. For example, if the force measured by the sensor 76 indicates the user is not applying enough force to a pedal 102, the treatment plan may indicate to reduce the required amount of force for an exercise.

It should be noted that, as the patient uses the treatment device 70, the user may use the patient interface 50 to enter input pertaining to a pain level experienced by the patient as the patient performs the treatment plan. For example, the user may enter a high degree of pain while pedaling with the pedals 102 set to a certain range of motion on the treatment device 70. The pain level may cause the range of motion to be dynamically adjusted based on the treatment plan. For example, the treatment plan may specify alternative range of motion settings if a certain pain level is indicated when the user is performing an exercise at a certain range of motion.

Figure 13:
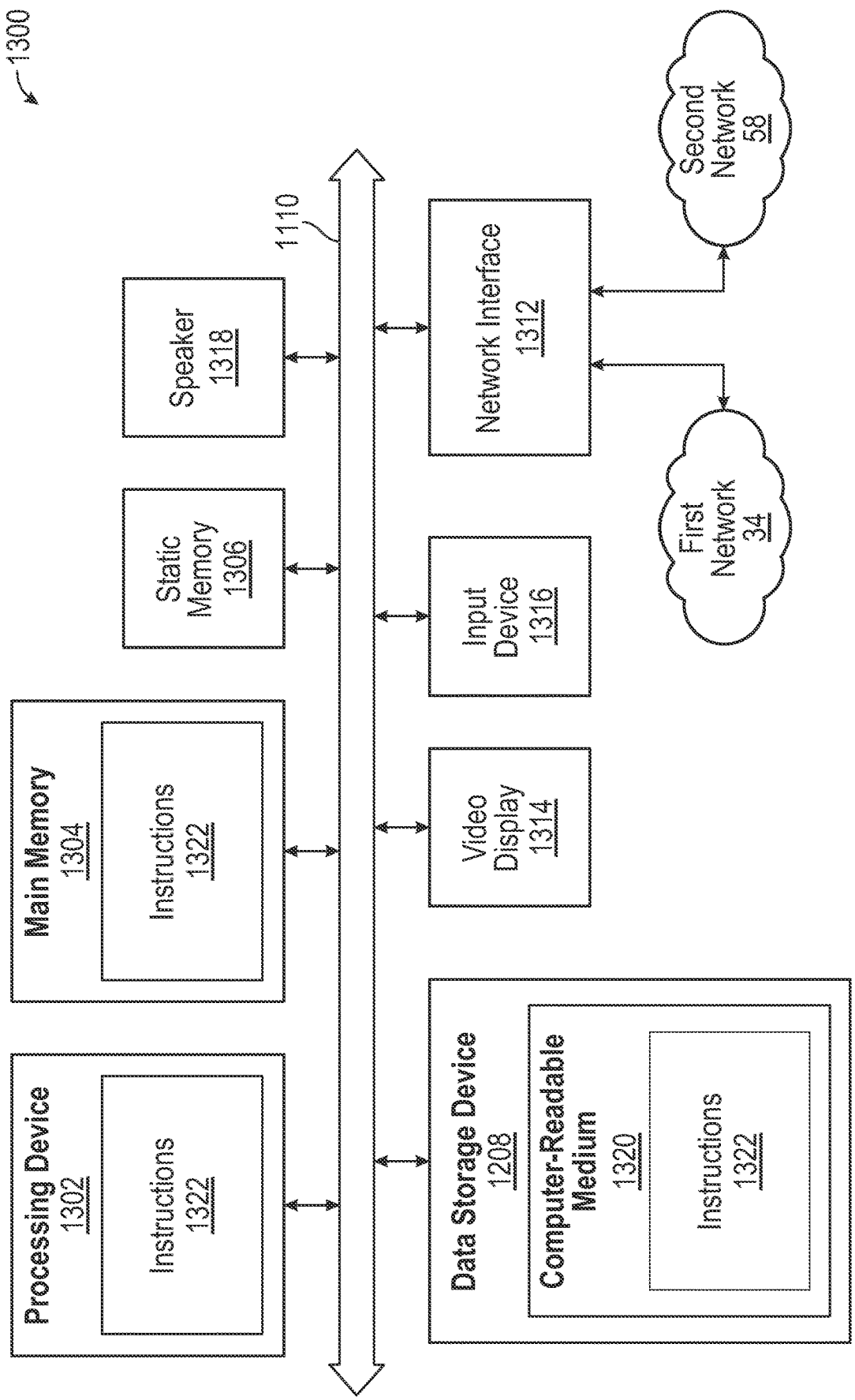
FIG. 13 generally illustrates a computer system according to the principles of the present disclosure.

FIG. 13 generally illustrates an example computer system 1300 which can perform any one or more of the methods described herein, in accordance with one or more aspects of the present disclosure. In one example, computer system 1300 may include a computing device and correspond to the assistance interface 94, reporting interface 92, supervisory interface 90, clinician interface 20, server 30 (including the AI engine 11), patient interface 50, ambulatory sensor 82, goniometer 84, treatment device 70, pressure sensor 86, or any suitable component of FIG. 1. The computer system 1300 may be capable of executing instructions implementing the one or more machine learning models 13 of the artificial intelligence engine 11 of FIG. 1. The computer system may be connected (e.g., networked) to other computer systems in a LAN, an intranet, an extranet, or the Internet, including via the cloud or a peer-to-peer network.

The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1300 includes a processing device 1302, a main memory 1304 (e.g., read-only memory (ROM), flash memory, solid state drives (SSDs), dynamic random access memory (DRAM) such as synchronous DRAM (SDRAM)), a static memory 1306 (e.g., flash memory, solid state drives (SSDs), static random access memory (SRAM)), and a data storage device 1308, which communicate with each other via a bus 1310.

Processing device 1302 represents one or more general-purpose processing devices such as a microprocessor, central processing unit, or the like. More particularly, the processing device 1302 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1402 may also be one or more special-purpose processing devices such as an application specific integrated circuit (ASIC), a system on a chip, a field programmable gate array (FPGA), a digital signal processor (DSP), network processor, or the like. The processing device 1402 is configured to execute instructions for performing any of the operations and steps discussed herein.

The computer system 1300 may further include a network interface device 1312. The computer system 1300 also may include a video display 1314 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 1316 (e.g., a keyboard and/or a mouse or a gaming-like control), and one or more speakers 1318 (e.g., a speaker). In one illustrative example, the video display 1314 and the input device(s) 1316 may be combined into a single component or device (e.g., an LCD touch screen).

The data storage device 1316 may include a computer-readable medium 1320 on which the instructions 1322 embodying any one or more of the methods, operations, or functions described herein is stored. The instructions 1322 may also reside, completely or at least partially, within the main memory 1304 and/or within the processing device 1302 during execution thereof by the computer system 1300. As such, the main memory 1304 and the processing device 1302 also constitute computer-readable media. The instructions 1322 may further be transmitted or received over a network via the network interface device 1312.

While the computer-readable storage medium 1320 is generally illustrated in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Clause 1. A computer-implemented system, comprising: a treatment device configured to be manipulated by a user while the user is performing a treatment plan; a patient interface comprising an output device configured to present telemedicine information associated with a telemedicine session; and a first computing device configured to: receive treatment data pertaining to the user while the user uses the treatment device to perform the treatment plan, wherein the treatment data comprises at least one of at least one characteristic of the user, at least one measurement pertaining to the user, at least one characteristic of the treatment device, and at least one aspect of the treatment plan; identify, using at least one aspect of the treatment data, at least one aspect of the at least one measurement pertaining to the user associated with a first treatment device mode of the treatment device; determine whether the at least one aspect of the at least one measurement pertaining to the user associated with the first treatment device mode of the treatment device correlates with at least one secondary condition of the user, wherein the at least one secondary condition of the user is not a primary condition for which the user is being treated; in response to a determination that the at least one aspect of the at least one measurement pertaining to the user associated with the first treatment device mode of the treatment device is correlated with the at least one secondary condition of the user, generate secondary condition information indicating at least the secondary condition; and write to an associated memory, for access at a second computing device of a healthcare provider, the secondary condition information.

Clause 2. The computer-implemented system of any clause herein, wherein the first computing device is further configured to determine whether the at least one aspect of the at least one measurement pertaining to the user associated with the first treatment device mode of the treatment device further includes instructions that cause the processor to: write to an associated memory, configured to be accessed by an artificial intelligence engine, the at least one aspect of the at least one measurement pertaining to the user associated with the first treatment device mode of the treatment device, the artificial intelligence engine being configured to use at least one machine learning model to generate, using the at least one aspect of the at least one measurement pertaining to the user associated with the first treatment device mode of the treatment device, at least one of secondary condition output prediction; and receive, from the artificial intelligence engine, the at least one secondary condition output prediction.

Clause 3. The computer-implemented system of any clause herein, wherein the artificial intelligence engine is further configured to use at least one machine learning model to generate, further using secondary condition information associated with other users, the at least one of secondary condition output prediction.

Clause 4. A method comprising: receiving treatment data pertaining to a user using a treatment device to perform a treatment plan, wherein the treatment data comprises at least one of at least one characteristic of the user, at least one measurement pertaining to the user, at least one characteristic of the treatment device, and at least one aspect of the treatment plan; identifying, using at least one aspect of the treatment data, at least one aspect of the at least one measurement pertaining to the user associated with a first treatment device mode of the treatment device; determining whether the at least one aspect of the at least one measurement pertaining to the user associated with the first treatment device mode of the treatment device correlates with at least one secondary condition of the user, wherein the at least one secondary condition of the user is not a primary condition for which the user is being treated; in response to a determination that the at least one aspect of the at least one measurement pertaining to the user associated with the first treatment device mode of the treatment device is correlated with the at least one secondary condition of the user, generating secondary condition information indicating at least the secondary condition; and writing to an associated memory, for access at a computing device of a healthcare provider, the secondary condition information.

Clause 5. The method of any clause herein, wherein determining whether the at least one aspect of the at least one measurement pertaining to the user associated with the first treatment device mode of the treatment device is correlated with the at least one secondary condition includes: writing to an associated memory, configured to be accessed by an artificial intelligence engine, the at least one aspect of the at least one measurement pertaining to the user associated with the first treatment device mode of the treatment device, the artificial intelligence engine being configured to use at least one machine learning model to generate, using the at least one aspect of the at least one measurement pertaining to the user associated with the first treatment device mode of the treatment device, at least one of secondary condition output prediction; and receiving, from the artificial intelligence engine, the at least one secondary condition output prediction.

Clause 6. The method of any clause herein, wherein the artificial intelligence engine is further configured to use at least one machine learning model to generate, further using secondary condition information associated with other users, the at least one of secondary condition output prediction.

Clause 7. The method of any clause herein, wherein the user and one or more other users belong to a user cohort.

Clause 8. The method of any clause herein, wherein the at least one machine learning model includes a deep network comprising multiple levels of non-linear operations.

Clause 9. The method of any clause herein, wherein at least some of the treatment data corresponds to at least some sensor data from a sensor associated with the treatment device.

Clause 10. The method of any clause herein, wherein at least some of the treatment data corresponds to at least some sensor data from a sensor associated with a wearable device worn by the user while using the treatment device.

Clause 11. The method of any clause herein, wherein at least one measurement includes, while the user uses the treatment device, at least one of a vital sign of the user, a respiration rate of the user, a heartrate of the user, a temperature of the user, an SpO2-measurement of a blood oxygen level of the user, and a blood pressure of the user.

Clause 12. The method of any clause herein, wherein the first treatment device mode of the treatment device includes one of an active assist treatment device mode, a passive mode, an active-assisted mode, a resistive mode, and an active mode.

Clause 13. A tangible, non-transitory computer-readable medium storing instructions that, when executed, cause a processing device to: receive treatment data pertaining to a user using a treatment device to perform a treatment plan, wherein the treatment data comprises at least one of at least one characteristic of the user, at least one measurement pertaining to the user, at least one characteristic of the treatment device, and at least one aspect of the treatment plan; identify, using at least one aspect of the treatment data, at least one aspect of the at least one measurement pertaining to the user associated with a first treatment device mode of the treatment device; determine whether the at least one aspect of the at least one measurement pertaining to the user associated with the first treatment device mode of the treatment device correlates with at least one secondary condition of the user, wherein the at least one secondary condition of the user is not a primary condition for which the user is being treated; in response to a determination that the at least one aspect of the at least one measurement pertaining to the user associated with the first treatment device mode of the treatment device is correlated with the at least one secondary condition of the user, generate secondary condition information indicating at least the secondary condition; and write to an associated memory, for access at a computing device of a healthcare provider, the secondary condition information.

Clause 14. The computer-readable medium of any clause herein, wherein the instructions causing the processing device to determine whether the at least one aspect of the at least one measurement pertaining to the user associated with the first treatment device mode of the treatment device further includes instructions that cause the processing device to: write to an associated memory, configured to be accessed by an artificial intelligence engine, the at least one aspect of the at least one measurement pertaining to the user associated with the first treatment device mode of the treatment device, the artificial intelligence engine being configured to use at least one machine learning model to generate, using the at least one aspect of the at least one measurement pertaining to the user associated with the first treatment device mode of the treatment device, at least one of secondary condition output prediction; and receive, from the artificial intelligence engine, the at least one secondary condition output prediction.

Clause 15. The computer-readable medium of any clause herein, wherein the artificial intelligence engine is further configured to use at least one machine learning model to generate, further using secondary condition information associated with other users, the at least one of secondary condition output prediction.

Clause 16. The computer-readable medium of any clause herein, wherein the user and one or more other users belong to a user cohort.

Clause 17. The computer-readable medium of any clause herein, wherein the at least one machine learning model includes a deep network comprising multiple levels of non-linear operations.

Clause 18. The computer-readable medium of any clause herein, wherein at least some of the treatment data corresponds to at least some sensor data from a sensor associated with the treatment device.

Clause 19. The computer-readable medium of any clause herein, wherein at least some of the treatment data corresponds to at least some sensor data from a sensor associated with a wearable device worn by the user while using the treatment device.

Clause 20. The computer-readable medium of any clause herein, wherein at least one measurement includes, while the user uses the treatment device, at least one of a vital sign of the user, a respiration rate of the user, a heartrate of the user, a temperature of the user, an SpO2-measurement of a blood oxygen level of the user, and a blood pressure of the user.

Clause 21. The computer-readable medium of any clause herein, wherein the first treatment device mode of the treatment device includes one of an active assist treatment device mode, a passive mode, an active-assisted mode, a resistive mode, and an active mode.

Clause 22. A system comprising: a processing device; and a memory including instructions that, when executed by the processor, cause the processor to: receive treatment data pertaining to a user using a treatment device to perform a treatment plan, wherein the treatment data comprises at least one of at least one characteristic of the user, at least one measurement pertaining to the user, at least one characteristic of the treatment device, and at least one aspect of the treatment plan; identify, using at least one aspect of the treatment data, at least one aspect of the at least one measurement pertaining to the user associated with a first treatment device mode of the treatment device; determine whether the at least one aspect of the at least one measurement pertaining to the user associated with the first treatment device mode of the treatment device correlates with at least one secondary condition of the user, wherein the at least one secondary condition of the user is not a primary condition for which the user is being treated; in response to a determination that the at least one aspect of the at least one measurement pertaining to the user associated with the first treatment device mode of the treatment device is correlated with the at least one secondary condition of the user, generate secondary condition information indicating at least the secondary condition; and write to an associated memory, for access at a computing device of a healthcare provider, the secondary condition information.

Clause 23. The system of any clause herein, wherein the instructions causing the processor to determine whether the at least one aspect of the at least one measurement pertaining to the user associated with the first treatment device mode of the treatment device further includes instructions that cause the processor to: write to an associated memory, configured to be accessed by an artificial intelligence engine, the at least one aspect of the at least one measurement pertaining to the user associated with the first treatment device mode of the treatment device, the artificial intelligence engine being configured to use at least one machine learning model to generate, using the at least one aspect of the at least one measurement pertaining to the user associated with the first treatment device mode of the treatment device, at least one of secondary condition output prediction; and receive, from the artificial intelligence engine, the at least one secondary condition output prediction.

Clause 24. The system of any clause herein, wherein the artificial intelligence engine is further configured to use at least one machine learning model to generate, further using secondary condition information associated with other users, the at least one of secondary condition output prediction.

Clause 25. The system of any clause herein, wherein the user and one or more other users below to a user cohort.

Clause 26. The system of any clause herein, wherein the at least one machine learning model includes a deep network comprising multiple levels of non-linear operations.

Clause 27. The system of any clause herein, wherein at least some of the treatment data corresponds to at least some sensor data from a sensor associated with the treatment device.

Clause 28. The system of any clause herein, wherein at least some of the treatment data corresponds to at least some sensor data from a sensor associated with a wearable device worn by the user while using the treatment device.

Clause 29. The system of any clause herein, wherein at least one measurement includes, while the user uses the treatment device, at least one of a vital sign of the user, a respiration rate of the user, a heartrate of the user, a temperature of the user, an SpO2-measurement of a blood oxygen level of the user, and a blood pressure of the user.

Clause 30. The system of any clause herein, wherein the first treatment device mode of the treatment device includes one of an active assist treatment device mode, a passive mode, an active-assisted mode, a resistive mode, and an active mode.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

The various aspects, embodiments, implementations, or features of the described embodiments can be used separately or in any combination. The embodiments disclosed herein are modular in nature and can be used in conjunction with or coupled to other embodiments.

Consistent with the above disclosure, the examples of assemblies enumerated in the following clauses are specifically contemplated and are intended as a non-limiting set of examples.

What is claimed is:

1. A computer-implemented system, comprising:
a treatment device configured to be manipulated by a user while the user is performing a treatment plan;
a patient interface comprising an output device configured to present telemedicine information associated with a telemedicine session; and
a first computing device configured to:
receive treatment data pertaining to the user while the user uses the treatment device to perform the treatment plan, wherein the treatment data comprises at least one of at least one characteristic of the user, at least one measurement pertaining to the user, at least one characteristic of the treatment device, and at least one aspect of the treatment plan;
identify, using at least one aspect of the treatment data, at least one aspect of the at least one measurement pertaining to the user associated with a first treatment device mode of the treatment device;
determine whether the at least one aspect of the at least one measurement pertaining to the user associated with the first treatment device mode of the treatment device correlates with at least one secondary condition of the user, wherein the at least one secondary condition of the user is not a primary condition for which the user is being treated;
in response to a determination that the at least one aspect of the at least one measurement pertaining to the user associated with the first treatment device mode of the treatment device is correlated with the at least one secondary condition of the user, generate secondary condition information indicating at least the secondary condition; and
write to an associated memory, for access at a second computing device of a healthcare provider, the secondary condition information.

2. The computer-implemented system of claim 1, wherein the first computing device is further configured to determine whether the at least one aspect of the at least one measurement pertaining to the user associated with the first treatment device mode of the treatment device further includes instructions that cause the processor to:
write to an associated memory, configured to be accessed by an artificial intelligence engine, the at least one aspect of the at least one measurement pertaining to the user associated with the first treatment device mode of the treatment device, the artificial intelligence engine being configured to use at least one machine learning model to generate, using the at least one aspect of the at least one measurement pertaining to the user associated with the first treatment device mode of the treatment device, at least one of secondary condition output prediction; and
receive, from the artificial intelligence engine, the at least one secondary condition output prediction.

3. The computer-implemented system of claim 1, wherein the artificial intelligence engine is further configured to use at least one machine learning model to generate, further using secondary condition information associated with other users, the at least one of secondary condition output prediction.

4. A method comprising:
receiving treatment data pertaining to a user using a treatment device to perform a treatment plan, wherein the treatment data comprises at least one of at least one characteristic of the user, at least one measurement pertaining to the user, at least one characteristic of the treatment device, and at least one aspect of the treatment plan;

identifying, using at least one aspect of the treatment data, at least one aspect of the at least one measurement pertaining to the user associated with a first treatment device mode of the treatment device;

determining whether the at least one aspect of the at least one measurement pertaining to the user associated with the first treatment device mode of the treatment device correlates with at least one secondary condition of the user, wherein the at least one secondary condition of the user is not a primary condition for which the user is being treated;

in response to a determination that the at least one aspect of the at least one measurement pertaining to the user associated with the first treatment device mode of the treatment device is correlated with the at least one secondary condition of the user, generating secondary condition information indicating at least the secondary condition; and writing to an associated memory, for access at a computing device of a healthcare provider, the secondary condition information.

5. The method of claim 4, wherein determining whether the at least one aspect of the at least one measurement pertaining to the user associated with the first treatment device mode of the treatment device is correlated with the at least one secondary condition includes:

writing to an associated memory, configured to be accessed by an artificial intelligence engine, the at least one aspect of the at least one measurement pertaining to the user associated with the first treatment device mode of the treatment device, the artificial intelligence engine being configured to use at least one machine learning model to generate, using the at least one aspect of the at least one measurement pertaining to the user associated with the first treatment device mode of the treatment device, at least one of secondary condition output prediction; and receiving, from the artificial intelligence engine, the at least one secondary condition output prediction.

6. The method of claim 5, wherein the artificial intelligence engine is further configured to use at least one machine learning model to generate, further using secondary condition information associated with other users, the at least one of secondary condition output prediction.

7. The method of claim 6, wherein the user and one or more other users belong to a user cohort.

8. The method of claim 5, wherein the at least one machine learning model includes a deep network comprising multiple levels of non-linear operations.

9. The method of claim 4, wherein at least some of the treatment data corresponds to at least some sensor data from a sensor associated with the treatment device.

10. The method of claim 4, wherein at least some of the treatment data corresponds to at least some sensor data from a sensor associated with a wearable device worn by the user while using the treatment device.

11. The method of claim 4, wherein at least one measurement includes, while the user uses the treatment device, at least one of a vital sign of the user, a respiration rate of the user, a heartrate of the user, a temperature of the user, an SpO2 measurement of the blood oxygen level of the user, and a blood pressure of the user.

12. The method of claim 4, wherein the first treatment device mode of the treatment device includes one of an active assist treatment device mode, a passive mode, an active-assisted mode, a resistive mode, and an active mode.

13. A tangible, non-transitory computer-readable medium storing instructions that, when executed, cause a processing device to:

receive treatment data pertaining to a user using a treatment device to perform a treatment plan, wherein the treatment data comprises at least one of at least one characteristic of the user, at least one measurement pertaining to the user, at least one characteristic of the treatment device, and at least one aspect of the treatment plan;

identify, using at least one aspect of the treatment data, at least one aspect of the at least one measurement pertaining to the user associated with a first treatment device mode of the treatment device;

determine whether the at least one aspect of the at least one measurement pertaining to the user associated with the first treatment device mode of the treatment device correlates with at least one secondary condition of the user, wherein the at least one secondary condition of the user is not a primary condition for which the user is being treated;

in response to a determination that the at least one aspect of the at least one measurement pertaining to the user associated with the first treatment device mode of the treatment device is correlated with the at least one secondary condition of the user, generate secondary condition information indicating at least the secondary condition; and write to an associated memory, for access at a computing device of a healthcare provider, the secondary condition information.

14. The computer-readable medium of claim 13, wherein the instructions causing the processing device to determine whether the at least one aspect of the at least one measurement pertaining to the user associated with the first treatment device mode of the treatment device further includes instructions that cause the processing device to:

write to an associated memory, configured to be accessed by an artificial intelligence engine, the at least one aspect of the at least one measurement pertaining to the user associated with the first treatment device mode of the treatment device, the artificial intelligence engine being configured to use at least one machine learning model to generate, using the at least one aspect of the at least one measurement pertaining to the user associated with the first treatment device mode of the treatment device, at least one of secondary condition output prediction; and receive, from the artificial intelligence engine, the at least one secondary condition output prediction.

15. The computer-readable medium of claim 14, wherein the artificial intelligence engine is further configured to use at least one machine learning model to generate, further using secondary condition information associated with other users, the at least one of secondary condition output prediction.

16. The computer-readable medium of claim 15, wherein the user and one or more other users belong to a user cohort.

17. The computer-readable medium of claim 14, wherein the at least one machine learning model includes a deep network comprising multiple levels of non-linear operations.

18. The computer-readable medium of claim 13, wherein at least some of the treatment data corresponds to at least some sensor data from a sensor associated with the treatment device.

19. The computer-readable medium of claim 13, wherein at least some of the treatment data corresponds to at least some sensor data from a sensor associated with a wearable device worn by the user while using the treatment device.

20. The computer-readable medium of claim 13, wherein at least one measurement includes, while the user uses the treatment device, at least one of a vital sign of the user, a respiration rate of the user, a heartrate of the user, a temperature of the user, an SpO2-measurement of a blood oxygen level of the user, and a blood pressure of the user.

21. The computer-readable medium of claim 13, wherein the first treatment device mode of the treatment device includes one of an active assist treatment device mode, a passive mode, an active-assisted mode, a resistive mode, and an active mode.

22. A system comprising:
a processing device; and
a memory including instructions that, when executed by the processor, cause the processor to:
receive treatment data pertaining to a user using a treatment device to perform a treatment plan, wherein the treatment data comprises at least one of at least one characteristic of the user, at least one measurement pertaining to the user, at least one characteristic of the treatment device, and at least one aspect of the treatment plan;
identify, using at least one aspect of the treatment data, at least one aspect of the at least one measurement pertaining to the user associated with a first treatment device mode of the treatment device;
determine whether the at least one aspect of the at least one measurement pertaining to the user associated with the first treatment device mode of the treatment device correlates with at least one secondary condition of the user, wherein the at least one secondary condition of the user is not a primary condition for which the user is being treated;
in response to a determination that the at least one aspect of the at least one measurement pertaining to the user associated with the first treatment device mode of the treatment device is correlated with the at least one secondary condition of the user, generate secondary condition information indicating at least the secondary condition; and
write to an associated memory, for access at a computing device of a healthcare provider, the secondary condition information.

23. The system of claim 22, wherein the instructions causing the processor to determine whether the at least one aspect of the at least one measurement pertaining to the user associated with the first treatment device mode of the treatment device further includes instructions that cause the processor to:
write to an associated memory, configured to be accessed by an artificial intelligence engine, the at least one aspect of the at least one measurement pertaining to the user associated with the first treatment device mode of the treatment device, the artificial intelligence engine being configured to use at least one machine learning model to generate, using the at least one aspect of the at least one measurement pertaining to the user associated with the first treatment device mode of the treatment device, at least one of secondary condition output prediction; and
receive, from the artificial intelligence engine, the at least one secondary condition output prediction.

24. The system of claim 23, wherein the artificial intelligence engine is further configured to use at least one machine learning model to generate, further using secondary condition information associated with other users, the at least one of secondary condition output prediction.

25. The system of claim 24, wherein the user and one or more other users below to a user cohort.

26. The system of claim 23, wherein the at least one machine learning model includes a deep network comprising multiple levels of non-linear operations.

27. The system of claim 22, wherein at least some of the treatment data corresponds to at least some sensor data from a sensor associated with the treatment device.

28. The system of claim 22, wherein at least some of the treatment data corresponds to at least some sensor data from a sensor associated with a wearable device worn by the user while using the treatment device.

29. The system of claim 22, wherein at least one measurement includes, while the user uses the treatment device, at least one of a vital sign of the user, a respiration rate of the user, a heartrate of the user, a temperature of the user, an SpO2-measurement of a blood oxygen level of the user, and a blood pressure of the user.

30. The system of claim 22, wherein the first treatment device mode of the treatment device includes one of an active assist treatment device mode, a passive mode, an active-assisted mode, a resistive mode, and an active mode.

* * * * *